(12) United States Patent
Hringsdottir et al.

(10) Patent No.: US 10,945,865 B2
(45) Date of Patent: Mar. 16, 2021

(54) PROSTHETIC SOCKET SEALING SYSTEM

(71) Applicant: OSSUR ICELAND EHF, Reykjavik (IS)

(72) Inventors: Hogna Hringsdottir, Reykjavik (IS); Dadi Granz, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 160 days.

(21) Appl. No.: 16/177,604

(22) Filed: Nov. 1, 2018

(65) Prior Publication Data

US 2019/0125553 A1 May 2, 2019

Related U.S. Application Data

(60) Provisional application No. 62/579,984, filed on Nov. 1, 2017.

(51) Int. Cl.
| | |
|---|---|
| *A61F 2/78* | (2006.01) |
| *A61F 2/80* | (2006.01) |
| A61F 2/74 | (2006.01) |
| A61F 2/60 | (2006.01) |
| A61F 2/50 | (2006.01) |

(52) U.S. Cl.
CPC ............... *A61F 2/80* (2013.01); *A61F 2/78* (2013.01); *A61F 2/7812* (2013.01); *A61F 2/60* (2013.01); *A61F 2002/5016* (2013.01); *A61F 2002/748* (2013.01); *A61F 2002/785* (2013.01); *A61F 2002/7875* (2013.01);
(Continued)

(58) Field of Classification Search
CPC ............. A61F 2/78; A61F 2/7812; A61F 2/80
See application file for complete search history.

(56) References Cited

U.S. PATENT DOCUMENTS

| | | |
|---|---|---|
| 980,457 A | 1/1911 | Toles |
| 1,398,824 A | 11/1921 | Abrams |
| (Continued) | | |

FOREIGN PATENT DOCUMENTS

| | | |
|---|---|---|
| AT | 369 978 B | 2/1983 |
| DE | 484 363 C | 10/1929 |
| (Continued) | | |

OTHER PUBLICATIONS

International Search Report and Written Opinion from PCT Application No. PCT/US2018/058624, dated Feb. 11, 2019.
(Continued)

*Primary Examiner* — Marcia L Watkins
(74) *Attorney, Agent, or Firm* — Workman Nydegger

(57) ABSTRACT

A prosthetic socket system includes a distal seal positionable between an interior surface of a prosthetic socket defining a pin bore and a distal end of a prosthetic liner carrying an attachment pin arranged to extend through the pin bore. The distal seal includes a base proximate to the attachment pin and defining an opening configured to receive and surround the attachment pin, a sealing portion extending distally from an outer radial portion of the base, and a variable clearance defined between the sealing portion and the base. The sealing portion is adapted to form a seal around the attachment pin and prevent fluid flow through the pin bore by deflecting relative to the base when the sealing portion engages the interior surface of the prosthetic socket.

11 Claims, 12 Drawing Sheets

(52) U.S. Cl.
CPC ... *A61F 2002/802* (2013.01); *A61F 2002/805* (2013.01); *A61F 2002/807* (2013.01)

(56) References Cited

U.S. PATENT DOCUMENTS

| | | | |
|---|---|---|---|
| 1,893,853 A | 1/1933 | Tullis | |
| 2,244,871 A | 6/1941 | Guinzburg | |
| 2,325,656 A | 8/1943 | Brophy | |
| 2,464,443 A | 3/1949 | Ganoe et al. | |
| 2,530,285 A | 11/1950 | Catranis | |
| 2,533,404 A | 12/1950 | Sharp et al. | |
| 2,634,424 A | 4/1953 | O'Gorman | |
| 2,671,225 A | 3/1954 | Schoene et al. | |
| 2,689,351 A | 9/1954 | Schindler | |
| 2,808,593 A | 10/1957 | Andersen | |
| 3,393,407 A | 7/1968 | Kandel | |
| 3,587,572 A | 6/1971 | Evans | |
| 3,671,980 A | 6/1972 | Baird | |
| 3,947,897 A | 4/1976 | Owens | |
| 4,128,903 A | 12/1978 | Marsh et al. | |
| 4,215,679 A | 8/1980 | Rustin | |
| 4,311,317 A | 1/1982 | Bartels | |
| 4,319,413 A | 3/1982 | Mattil | |
| 4,347,204 A | 8/1982 | Takagi et al. | |
| 4,474,573 A | 10/1984 | Detty | |
| 4,635,626 A | 1/1987 | Lerman | |
| 4,738,249 A | 4/1988 | Linman et al. | |
| 4,767,735 A | 8/1988 | Ewen et al. | |
| 4,885,828 A | 12/1989 | Kozlowski | |
| 4,908,037 A | 3/1990 | Ross | |
| 4,923,474 A | 5/1990 | Klasson et al. | |
| 5,007,937 A | 4/1991 | Fishman et al. | |
| 5,055,528 A | 10/1991 | Kioka et al. | |
| 5,122,583 A | 6/1992 | Ewen et al. | |
| 5,139,523 A | 8/1992 | Paton et al. | |
| 5,163,965 A | 11/1992 | Rasmusson et al. | |
| 5,169,161 A | 12/1992 | Jones | |
| 5,226,918 A | 7/1993 | Silagy et al. | |
| 5,244,716 A | 9/1993 | Thornton et al. | |
| 5,314,496 A | 5/1994 | Harris et al. | |
| 5,376,129 A | 12/1994 | Faulkner et al. | |
| 5,376,131 A | 12/1994 | Lenze et al. | |
| 5,387,245 A | 2/1995 | Fay et al. | |
| 5,549,709 A | 8/1996 | Caspers | |
| 5,571,208 A | 11/1996 | Caspers | |
| 5,571,209 A | 11/1996 | Brown, Sr. | |
| 5,593,454 A | 1/1997 | Helmy | |
| 5,658,353 A | 8/1997 | Layton | |
| 5,702,489 A | 12/1997 | Slemker | |
| 5,718,925 A | 2/1998 | Kristinsson et al. | |
| 5,728,168 A | 3/1998 | Laghi et al. | |
| 5,728,170 A | 3/1998 | Becker et al. | |
| 5,735,906 A | 4/1998 | Caspers | |
| 5,830,237 A | 11/1998 | Kania | |
| 5,885,674 A | 3/1999 | Maemoto et al. | |
| 5,888,216 A | 3/1999 | Haberman | |
| 5,888,230 A | 3/1999 | Helmy | |
| 5,888,234 A * | 3/1999 | Littig | A61F 2/76 623/38 |
| 5,904,722 A | 5/1999 | Caspers | |
| 5,931,872 A | 8/1999 | Lohmann | |
| 5,972,036 A | 10/1999 | Kristinsson et al. | |
| 5,980,577 A | 11/1999 | Radis et al. | |
| 6,076,284 A | 6/2000 | Terlizzi | |
| 6,136,039 A | 10/2000 | Kristinsson et al. | |
| 6,149,691 A | 11/2000 | Fay et al. | |
| 6,171,431 B1 | 1/2001 | Gallagher, Jr. et al. | |
| 6,231,616 B1 | 5/2001 | Helmy | |
| 6,231,617 B1 | 5/2001 | Fay | |
| 6,267,787 B1 * | 7/2001 | Capper | A61F 2/76 623/33 |
| 6,273,918 B1 | 8/2001 | Yuhasz et al. | |
| 6,287,345 B1 | 9/2001 | Slemker et al. | |
| 6,361,568 B1 | 3/2002 | Hoerner | |
| 6,368,357 B1 | 4/2002 | Schon et al. | |
| 6,406,499 B1 | 6/2002 | Kania | |
| 6,468,938 B1 | 10/2002 | Govoni et al. | |
| 6,485,776 B2 | 11/2002 | Janusson et al. | |
| 6,508,842 B1 | 1/2003 | Caspers | |
| 6,544,292 B1 | 4/2003 | Laghi | |
| 6,554,868 B1 | 4/2003 | Caspers | |
| 6,585,774 B2 | 7/2003 | Dean, Jr. et al. | |
| 6,626,952 B2 | 9/2003 | Janusson et al. | |
| 6,645,253 B2 | 11/2003 | Caspers | |
| 6,706,364 B2 | 3/2004 | Janusson et al. | |
| 6,726,726 B2 | 4/2004 | Caspers | |
| 6,761,742 B2 | 7/2004 | Caspers | |
| 6,797,008 B1 | 9/2004 | Arbogast et al. | |
| 6,852,269 B2 | 2/2005 | Eberle et al. | |
| 6,926,742 B2 | 8/2005 | Caspers et al. | |
| 6,929,125 B1 | 8/2005 | Seamans | |
| 6,964,688 B1 | 11/2005 | Kania | |
| 7,001,563 B2 | 2/2006 | Janusson et al. | |
| 7,025,793 B2 | 4/2006 | Egilsson | |
| 7,118,602 B2 | 10/2006 | Bjarnason | |
| 7,144,429 B2 | 12/2006 | Carstens | |
| 7,169,188 B2 | 1/2007 | Carstens | |
| 7,169,189 B2 | 1/2007 | Bjarnason et al. | |
| 7,235,108 B2 | 6/2007 | Carstens | |
| 7,291,182 B1 | 11/2007 | Kania | |
| 7,351,264 B2 | 4/2008 | Wilson | |
| 7,427,297 B2 | 9/2008 | Patterson et al. | |
| 7,592,286 B2 | 9/2009 | Morini et al. | |
| 7,749,281 B2 | 7/2010 | Egilsson | |
| 7,771,487 B2 | 8/2010 | Mantelmacher | |
| 7,909,884 B2 | 3/2011 | Egilsson et al. | |
| 8,034,120 B2 | 10/2011 | Egilsson et al. | |
| 8,052,760 B2 | 11/2011 | Egilsson et al. | |
| 8,097,043 B2 | 1/2012 | Egilsson | |
| 8,206,459 B1 | 6/2012 | Lock et al. | |
| 8,372,159 B2 | 2/2013 | MacKenzie | |
| 8,894,719 B2 | 11/2014 | Egilsson et al. | |
| 8,911,506 B2 | 12/2014 | Egilsson et al. | |
| 9,056,022 B2 | 6/2015 | Egilsson et al. | |
| 9,060,885 B2 | 6/2015 | Egilsson et al. | |
| 9,066,821 B2 | 6/2015 | Egilsson et al. | |
| 9,295,567 B2 | 3/2016 | Egilsson et al. | |
| 9,566,175 B2 | 2/2017 | Halldorsson | |
| 9,603,726 B2 | 3/2017 | Egilsson et al. | |
| 9,707,106 B2 | 7/2017 | Egilsson et al. | |
| 2001/0005798 A1 | 6/2001 | Caspers | |
| 2001/0016781 A1 | 8/2001 | Caspers | |
| 2002/0040248 A1 | 4/2002 | Karason | |
| 2002/0087215 A1 | 7/2002 | Caspers | |
| 2002/0091449 A1 | 7/2002 | Caspers et al. | |
| 2002/0099450 A1 | 7/2002 | Dean, Jr. et al. | |
| 2002/0165619 A1 | 11/2002 | Hellberg | |
| 2002/0183859 A1 | 12/2002 | Houser | |
| 2003/0181989 A1 | 9/2003 | Eberle et al. | |
| 2003/0191539 A1 | 10/2003 | Caspers | |
| 2004/0012158 A1 | 1/2004 | Neuhaus | |
| 2004/0024322 A1 | 2/2004 | Caspers | |
| 2004/0030411 A1 | 2/2004 | Caspers | |
| 2004/0040248 A1 | 3/2004 | Vilnes | |
| 2004/0098136 A1 | 5/2004 | Caspers | |
| 2004/0122528 A1 | 6/2004 | Egilsson | |
| 2004/0143345 A1 | 7/2004 | Caspers | |
| 2004/0167638 A1 | 8/2004 | Caspers | |
| 2004/0181290 A1 | 9/2004 | Caspers | |
| 2004/0236434 A1 | 11/2004 | Carstens | |
| 2004/0243251 A1 | 12/2004 | Carstens | |
| 2004/0243252 A1 | 12/2004 | Carstens | |
| 2005/0101693 A1 | 5/2005 | Arbogast et al. | |
| 2005/0216095 A1 | 9/2005 | Egilsson | |
| 2005/0240282 A1 | 10/2005 | Rush et al. | |
| 2005/0240283 A1 | 10/2005 | Kania | |
| 2005/0267598 A1 | 12/2005 | Bjarnason et al. | |
| 2005/0267599 A1 | 12/2005 | Bjarnason | |
| 2006/0212128 A1 | 9/2006 | Nachbar | |
| 2006/0293762 A1 | 12/2006 | Schulman et al. | |
| 2007/0005149 A1 | 1/2007 | Egilsson et al. | |
| 2007/0021295 A1 | 1/2007 | Morini et al. | |
| 2007/0027556 A1 | 2/2007 | Wilson | |
| 2007/0043450 A1 | 2/2007 | Pickering et al. | |

(56) References Cited

U.S. PATENT DOCUMENTS

| | | |
|---|---|---|
| 2007/0061017 A1 | 3/2007 | Wilson |
| 2007/0123998 A1 | 5/2007 | Egilsson et al. |
| 2007/0179606 A1 | 8/2007 | Huyghe et al. |
| 2008/0086218 A1 | 4/2008 | Egilsson |
| 2008/0147202 A1 | 6/2008 | Danzig et al. |
| 2008/0188949 A1 | 8/2008 | MacKenzie |
| 2008/0221705 A1 | 9/2008 | Scussel |
| 2008/0221706 A1 | 9/2008 | Scussel et al. |
| 2008/0269914 A1 | 10/2008 | Coppens et al. |
| 2009/0036999 A1 | 2/2009 | Egilsson et al. |
| 2009/0069171 A1 | 3/2009 | Sagae |
| 2009/0157196 A1 | 6/2009 | Danzig et al. |
| 2009/0182435 A1 | 7/2009 | Haberman |
| 2009/0198346 A1 | 8/2009 | Perkins et al. |
| 2009/0240344 A1 | 9/2009 | Colvin et al. |
| 2009/0306791 A1 | 12/2009 | Slemker et al. |
| 2010/0070051 A1 | 3/2010 | Carstens |
| 2010/0185300 A1 | 7/2010 | MacKenzie |
| 2010/0249950 A1 | 9/2010 | Bielefeld |
| 2010/0274364 A1 | 10/2010 | Pacanowsky et al. |
| 2010/0318196 A1 | 12/2010 | Egilsson |
| 2011/0029096 A1 | 2/2011 | Laghi |
| 2011/0035027 A1 | 2/2011 | McCarthy |
| 2011/0054635 A1 | 3/2011 | Watts |
| 2011/0071649 A1 | 3/2011 | McKinney |
| 2011/0077748 A1 | 3/2011 | Egilsson et al. |
| 2011/0118854 A1 | 5/2011 | Halldorsson |
| 2012/0041568 A1 | 2/2012 | MacKenzie |
| 2012/0095571 A1 | 4/2012 | Gunnarsson et al. |
| 2013/0053982 A1 | 2/2013 | Halldorsson |
| 2013/0138224 A1 | 5/2013 | MacKenzie |
| 2013/0173020 A1* | 7/2013 | Slemker .................. A61F 2/78 623/34 |
| 2013/0197670 A1 | 8/2013 | MacKenzie |
| 2013/0331952 A1 | 12/2013 | Halldorsson et al. |
| 2015/0142133 A1 | 5/2015 | Egilsson et al. |
| 2015/0202060 A1 | 7/2015 | Muller et al. |
| 2016/0106557 A1 | 4/2016 | Egilsson et al. |
| 2017/0105853 A1 | 4/2017 | Jonsson et al. |
| 2017/0151073 A1 | 6/2017 | Halldorsson |
| 2017/0209290 A1 | 7/2017 | Birgisdottir et al. |
| 2017/0304085 A1 | 10/2017 | Kurth |

FOREIGN PATENT DOCUMENTS

| | | |
|---|---|---|
| DE | 745 981 C | 5/1944 |
| DE | 813 190 C | 9/1951 |
| DE | 1 795 809 U | 9/1959 |
| DE | 2 060 239 A1 | 6/1972 |
| DE | 2 127 269 A1 | 12/1972 |
| DE | 2 540 138 A1 | 3/1977 |
| DE | 2 544 446 A1 | 4/1977 |
| DE | 3 221 920 A1 | 4/1983 |
| DE | 3 508 919 A1 | 9/1986 |
| DE | 9 419 208 U1 | 1/1995 |
| EP | 0 631 765 A1 | 1/1995 |
| EP | 1 572 043 A2 | 9/2005 |
| EP | 2353550 A1 | 8/2011 |
| EP | 2745807 A1 | 6/2014 |
| EP | 2815728 A1 | 12/2014 |
| FR | 2 420 335 A1 | 10/1979 |
| FR | 2 539 616 A1 | 7/1984 |
| FR | 2 828 093 A1 | 2/2003 |
| GB | 263 377 A | 12/1926 |
| GB | 267 988 A | 3/1927 |
| GB | 269606 A | 4/1927 |
| GB | 826 041 A | 12/1959 |
| GB | 2 069 847 A | 9/1981 |
| GB | 2 087 727 A | 6/1982 |
| JP | H0623406 A | 2/1994 |
| JP | H07109314 A | 4/1995 |
| JP | H7-155343 A | 6/1995 |
| JP | H9-104714 A | 4/1997 |
| JP | 2637076 B2 | 8/1997 |
| JP | 2740503 B2 | 4/1998 |
| JP | H10-182740 A | 7/1998 |
| JP | 2001-055413 A | 2/2001 |
| JP | 2002-500697 A | 1/2002 |
| JP | 2006-176565 A | 7/2006 |
| JP | 2006-316160 A | 11/2006 |
| JP | 2006-528271 A | 12/2006 |
| JP | 3984304 B2 | 10/2007 |
| JP | 2011206118 A | 10/2011 |
| WO | 97/34548 A2 | 9/1997 |
| WO | 00/74611 A2 | 12/2000 |
| WO | 01/54631 A1 | 8/2001 |
| WO | 01/67842 A1 | 9/2001 |
| WO | 02/26158 A2 | 4/2002 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |
| WO | 2004/060136 A2 | 7/2004 |
| WO | 2010/085336 A1 | 7/2010 |
| WO | 2013/005735 A1 | 1/2013 |
| WO | 2015073793 A1 | 5/2015 |

OTHER PUBLICATIONS

"Silicone-Only Suspension (SOS) with Socket-Loc and the Ring for the Lower Limb", found at, http://www.oandp.org/ipo/library/1995_01_002.asp. Journal of Prosthetics and Orthotics 1995;vol. 7, No. 1, p. 2.

Iceross Comfort Locking/Cushion Product Information Brochure, Mar. 27, 2009, 3 Pages.

Iceross Dermo, Product Information Sheets from Internet, http://www.ossur.com/prosthetics/liners/dermo, Mar. 27, 2009, 2 Sheets.

Military inStep: Prosthetic Socks and Liners, Product Information Sheets from Internet, http://www.amputee-coalition.org/military-instep/prosthetic-socks, Mar. 27, 2009, 3 Pages.

Prosthetic & Orthotic Update NewsLetter, No. 32, Internet Search Conducted Mar. 27, 2009, 4 Pages.

Walopur Platilon U, Product Information Brochure of Epurex Films GmbH & Co., KG, Internet Search Result Conducted Mar. 27, 2009, 2 Pages.

International Search Report and Written Opinion Issued in PCT/US2012/051645, dated Dec. 3, 2012.

Supplementary EP Search Report from EP Application No. 07837275.2, dated Feb. 19, 2014, 6 pages.

Extended European Search Report from EP Application No. 14161004.8, dated May 22, 2014, 6 pages.

Extended European Search Report from Corresponding Application No. 14163512.8, dated Jul. 30, 2014.

ESP Opti-Seal, Product Installation Instructions, http://www.wearesp.com, Downloaded Dec. 12, 2014, 1 page.

ESP Opti-Seal, "The Most Versatile Suspension System Availiable", www.wearesp.com, Downloaded Dec. 12, 2014, 2 pages.

ESP Secure-Ring System (SRS), http://www.wearesp.com, Downloaded Dec. 12, 2014, 1 page.

ESP Secure-Ring System (SRS), Product Instructions Sheet, http://www.wearesp.com, downloaded Dec. 12, 2014, 2 pages.

International Search Report from PCT Application No. PCT/US2016/055269, dated Jan. 4, 2017.

Eshraghi et al., "Gait Biomechanics of Individuals with Transtibial Amputation: Effect of Suspension System", PLOS ONE, vol. 9, Issue. 5, May 2014, 12 Pages.

Eshraghi et al., "Pistoning Assessment in Lower Limb Prosthetic Sockets", Prosthetics and Orthotics International, vol. 36, No. 1, 2012, pp. 15-24.

Gholizadeh et al., "Transtibial Prosthesis Suspension Systems: Systematic Review of Literature", Clinical Biomechanics vol. 29, 2014, pp. 87-97.

"Prosthetics Product Catalogue", Medi Prosthetics, www.medi-prosthetics.com, Jan. 2016, 184 pages.

"Verwendung und Verklebung Des LITE Vakuum-Ringes 5W700: Usage and Gluing of the 5W700 LITE Vacuum Ring", Wagner Polymertechnik GMBH, Sep. 6, 2016, 4 Pages.

(56) References Cited

OTHER PUBLICATIONS

International Search Report from PCT Application No. PCT/US2017/029063, dated Jul. 21, 2017.
"Slick SIL LSR," Surface Solutions Group LLC, retrieved from www.surfacesolutionsgroup.com on Mar. 30, 2017, 1 Page.

* cited by examiner

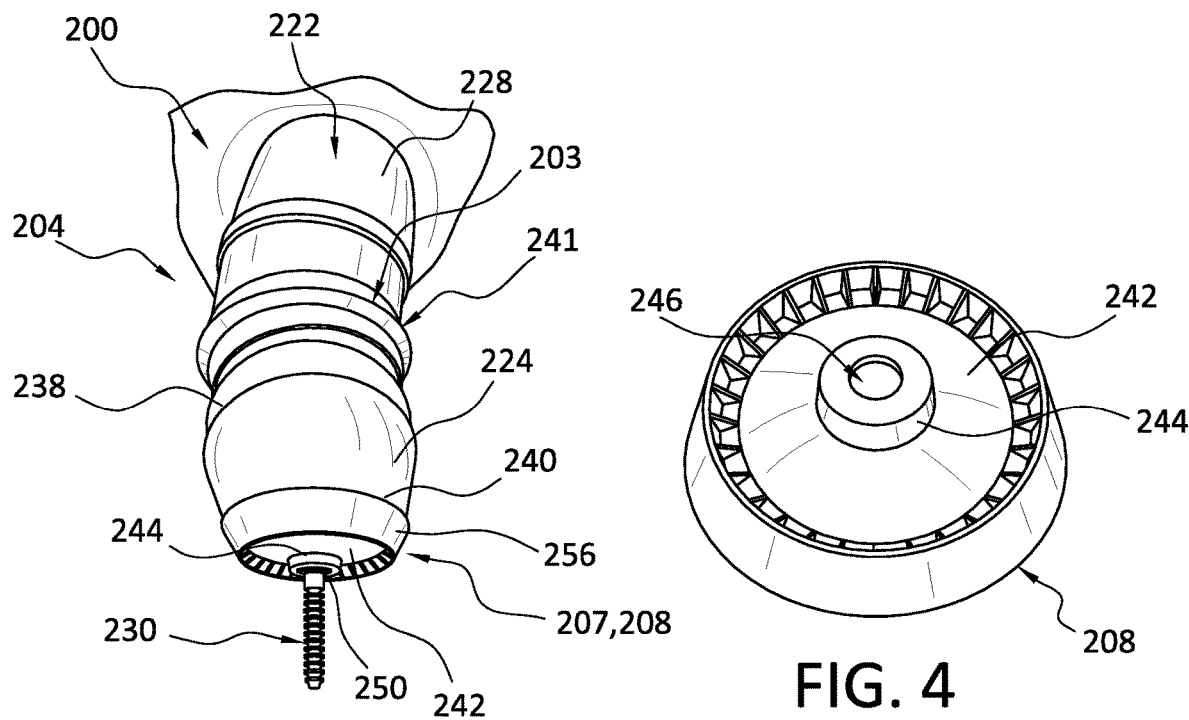
FIG. 2
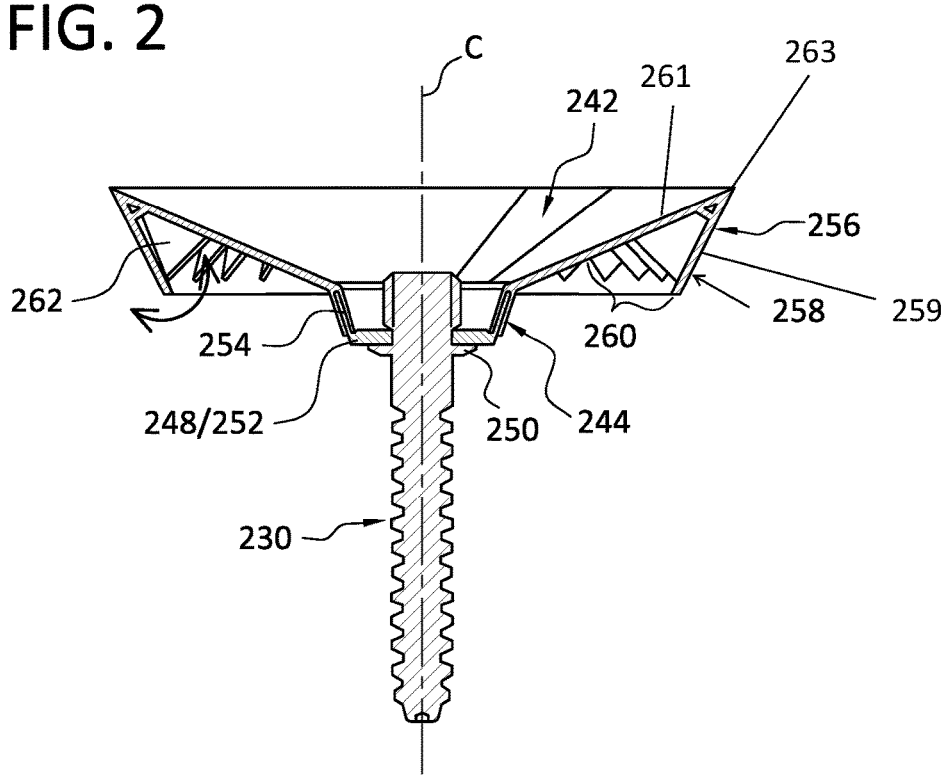
FIG. 4
FIG. 3

PROSTHETIC SOCKET SEALING SYSTEM

TECHNICAL FIELD

The disclosure relates to prosthetic socket systems including one or more suspension mechanisms for securing a prosthetic socket to a residual limb.

BACKGROUND

A typical prosthetic leg and foot includes a socket, pylon, and foot. A socket is commonly referred to as the portion of a prosthesis that fits around and envelops a residual limb or stump, and to which prosthetic components, such as a foot, are attached. The socket must fit closely to the residual limb to provide a firm connection and support but must also be sufficiently loose to allow for circulation. In combination with proper fitting, the socket must transfer loads from the residual limb to the ground in a comfortable manner.

To increase comfort, it may be provided that a prosthetic liner is arranged between the socket and the residual limb. In general, the prosthetic liner includes an elastomeric body having a closed distal end and an open proximal end that is pulled or rolled over the residual limb. The prosthetic liner adheres to the residual limb surface and generates the connection between the residual limb and the socket.

Different mechanisms exist for holding the socket on the residual limb during use of the prosthesis. For instance, locking suspension provides an attachment pin at the distal end of the prosthetic liner and a corresponding prosthetic attachment lock at the distal end of the socket, which mechanically locks the prosthetic liner to the socket after insertion into the socket. While providing a secure connection between the socket and the residual limb, this mechanical lock can lead to skin problems and stability issues. For instance, the attachment pin only attaches to the socket in the distal end of the socket at a point, which can cause unwanted movement as the prosthetic liner stretches when taking up loads during gait. This point connection can result in "milking" where the distal end of the residual limb is pulled a little in every step, which, in turn, can lead to skin problems, such as stretching of the tissues at the limb residuum and swelling, inflammation, distortion, and pain, among others.

Mechanical locking systems can also result in "pistoning" or exaggerated in-and-out motion of the residual limb in the socket, which, in turn, can cause additional friction and shear that may lead to skin chafing and blistering. Such locking suspension systems may additionally lead to stability or rotational issues if the socket is not fitting tightly enough.

Another mechanism for attaching a socket to a residual limb resides in what is known as a vacuum lock or vacuum suspension, in which the socket seals airtight against the prosthetic liner and air present in the space between the prosthetic liner and the socket is pulled or forced out. This creates a suction tending to retain the residual limb within the socket, reduce pistoning, and improve stability. Disadvantageously, however, vacuum suspension can only be used with sockets that are airtight and thus is considered a less reliable suspension mechanism. For instance, the strength and reliability of the seal attaching the socket to the residual limb can be impaired and/or broken due to irregular loading of the socket by the user, excessive relative movement between the prosthetic liner and the socket, perspiration, and/or other factors. This can compromise suspension and, in the worst case, can cause the prosthesis to fall off, which, in turn, increases the likelihood of injury and user doubt. In addition, fitting a socket to a user for vacuum suspension is generally more complicated and expensive than for mechanical locking suspension.

Additionally, traditional vacuum suspension systems may not be available to all users; for example, users with shorter residual limbs may not be able to use existing vacuum suspension systems because of air channeling through the shorter distance, leading to loss of vacuum and potentially catastrophic failure of the attachment. Vacuum systems may further be undesirable or impractical for elderly users.

Thus, existing prosthetic socket systems must choose between two imperfect option: a mechanical lock that is reliable but unstable and uncomfortable against a user's skin, or a vacuum lock that is more comfortable and stable but less reliable. Accordingly, there is a need for an improved prosthetic socket system that provides more reliable and stable prosthetic suspension with reduced risk of skin problems and other injuries.

SUMMARY

Embodiments of the present disclosure can include a prosthetic socket system having a distal seal positionable between an interior surface of a prosthetic socket defining a pin bore and a distal end of a prosthetic liner carrying an attachment pin arranged to extend through the pin bore. The distal seal includes a base proximate to the attachment pin and defining an opening configured to receive and surround the attachment pin, a sealing portion extending distally from an outer radial portion of the base, and a variable clearance defined between the sealing portion and the base.

When the prosthetic liner is inserted in the socket, the variable clearance and a flexibility of the distal seal allow the sealing portion to deflect and deform relative to the base when the sealing portion engages a distal interior surface of the socket, bridging a seal between the distal outer surface of the prosthetic liner and the distal interior surface of the socket. This seals off the attachment pin extending through the pin bore of the socket, preventing air from entering or exiting the socket cavity via the pin bore. The variable clearance and flexibility of the distal seal help the distal seal compensate for relative movement between the distal interior surface of the socket and the prosthetic liner by allowing the sealing portion to better move with and exert pressure against the distal interior surface of the socket to improve the seal.

The distal seal, with its variable clearance and flexibility, also isolates the mechanical lock between the prosthetic liner and the portion of the socket extending from the socket cavity proximal to the distal seal, which, in turn, allows for the formation of a vacuum lock between the prosthetic liner and the socket. The vacuum lock can provide a larger attachment area or attachment length between the prosthetic liner and the socket than that provided by the attachment pin alone. This reduces the likelihood of problems that can result when the attachment pin pulls on the distal end of the prosthetic liner.

For instance, the larger attachment area of the vacuum lock presses or holds the socket and the prosthetic liner together over a larger area of the prosthetic liner, not just at the attachment pin, reducing the likelihood of pistoning and milking between the residual limb and the socket. It also helps improve rotational control and stability of the prosthetic socket system because the socket and the prosthetic liner are more likely to move together rather than rotate or displace relative to one another during use of the prosthetic socket system. Further, if the vacuum lock is unexpectedly reduced or lost, the mechanical lock between the attachment pin and the socket reliably keeps the socket attached to the prosthetic liner, preventing the socket from falling of the residual limb. In this way, the prosthetic socket system of the disclosure achieves the benefits of mechanical locking and vacuum locking systems while avoiding the respective drawbacks of each system.

Moreover, the vacuum and mechanical locks or dual suspension mechanisms of the present disclosure can benefit a wide range of users. For instance, below-the-knee amputees can comfortably use the prosthetic socket system to enjoy the comfort and stability of vacuum suspension without having to worry about their prosthesis falling off. Furthermore, higher activity users can move more confidently using the prosthetic socket system in challenging situations like cycling, running, and climbing, owing to the enhanced security offered by the dual suspension mechanisms. In addition, elderly or lower activity users can comfortably and confidently use the prosthetic socket system without having to worry about undesirable pistoning or about a loss of suspension while the user is sitting or kneeling, and further without experiencing the skin problems and pain of existing systems.

The dual suspension mechanisms of the present disclosure additionally can benefit clinicians in the recommendation and fitting of prosthetic socket systems. Clinicians often do not feel confident providing more elderly patients with vacuum suspension because the patient tends to worry about the socket falling off. With the dual suspension systems of the present disclosure, clinicians can offer these patients a safe solution and at the same time the benefits of vacuum suspension. Clinicians also tend to shorten the fit of a socket on a residual limb using a locking liner because of friction concerns associated with undesirable pistoning. With the dual suspension mechanisms of the present disclosure which minimize such drawbacks, clinicians can align the residual limb length more correctly with a length of the socket, not shorter per certain existing systems and practices to compensate for pistoning, because of the reduced risk of pistoning. This helps improve the fit and support of the socket.

Exemplary embodiments of the present disclosure further describe locking systems that consolidate a vacuum seal and a mechanical locking system into a single prosthetic socket system device or component, which device or component further comprises a release mechanism allowing a user to intuitively and simply doff the prosthetic socket system through a single motion, minimizing the cost and complexity of the prosthetic socket system according to the disclosure. Other embodiments describe an improved prosthetic socket system for allowing fluid flow in desired directions and patterns within the prosthetic socket system

BRIEF DESCRIPTION OF THE DRAWINGS

These and other features, aspects, and advantages of the present disclosure will become better understood regarding the following description, appended claims, and accompanying drawings.

FIG. 2 shows a perspective view of a prosthetic socket system according to another embodiment.

FIG. 3 shows a cross section of the distal seal of FIG. 2 in an elevational view.

FIG. 4 shows the distal seal of FIG. 2 in a perspective view.

Figure 1:
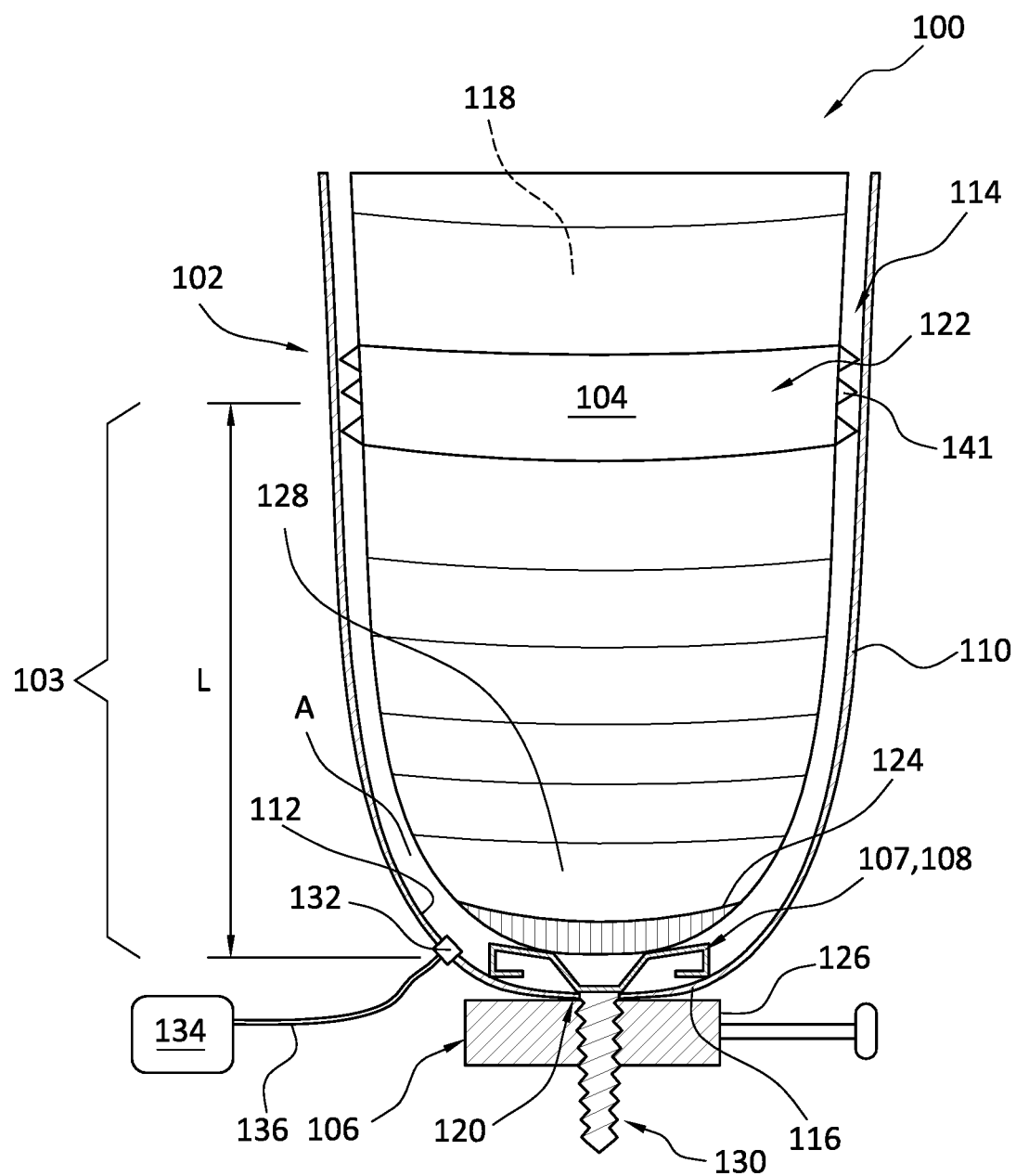
FIG. 1 shows an elevational view of a cross section of a prosthetic socket system according to an embodiment.

The drawing figures are not necessarily drawn to scale, but instead are drawn to provide a better understanding of the components, and are not intended to be limiting in scope, but to provide exemplary illustrations. The figures illustrate exemplary configurations of prosthetic socket systems, and in no way limit the structures or configurations of a prosthetic socket system and components according to the present disclosure

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

Embodiments of the present disclosure advantageously combine vacuum and locking suspension to enhance the reliability, stability, and comfort of the attachment between the residual limb and the socket. FIG. 1 illustrates a prosthetic socket system 100 according to an embodiment including a socket 102, a prosthetic liner 104, and a prosthetic lock assembly 106. The socket 102 has an outer surface 110 and an opposing interior surface 112 defining a socket cavity 114. The socket cavity 114 includes an open proximal end and a distal end 116. The open proximal end is adapted to receive a distal portion of a residual limb 118 to inserted in the socket cavity 114. The distal end 116 includes a pin bore 120 extending therethrough.

The prosthetic liner 104 is configured to be donned on the residual limb 118 and positioned in the socket cavity 114. Typical liners are made of soft, stretch material and protect the residual limb 118 and act as an interface between the harder, weight bearing socket 102 and the skin of the residual limb 118. The prosthetic liner 104 includes a liner body 122 having a proximal end, which is open, and a distal end 124, which is closed. The liner body 122 defines an inner surface that interfaces with the skin, and an outer surface 128 opposing the inner surface. The liner body 122 can be formed of a polymeric or elastomeric material like silicone, copolymer gel, polyurethane, combinations thereof, or any other suitable material.

An attachment pin 130 is secured to the distal end 124 of the prosthetic liner 104. The attachment pin 130 can define a plurality of notches or can be smooth. The attachment pin 130 may be mounted to the prosthetic liner 104 by being molded or threaded onto the distal end 124 of the prosthetic liner 104. The attachment pin 130 is positioned to extend through the pin bore 120 of the socket 102 and thus through the distal end 116 of the socket 102.

The attachment pin 130 engages the prosthetic lock assembly 106 that may or may not be laminated into the socket 102. The prosthetic lock assembly 106 is arranged to connect to prosthetic components (e.g., a pylon system, socket adapters, or a prosthetic foot) and effectively couples the prosthetic liner 104, the socket 102, and the other components together. When the attachment pin 130 passes through the pin bore 120 of the socket 102, the prosthetic lock assembly 106 can receive and lock the attachment pin 130 therein, which, in turn, mechanically couples the prosthetic liner 104 to the socket 102. This mechanical lock or attachment of the prosthetic liner 104 to the socket 102 can be released via a release mechanism 126 of the prosthetic lock assembly 106. The mechanical lock thus provides a user with safe and reliable suspension.

In addition to the mechanical lock provided by the prosthetic lock assembly 106, the prosthetic socket system 100 can include a sealing system 103 configured to isolate a distal end portion of the socket cavity 114 from atmosphere after the prosthetic liner 104 has been fully inserted within the socket 102, which, in turn allows a vacuum or suction to be generated between the prosthetic liner 104 and the socket 102 for vacuum suspension in supplement to the mechanical lock provided by the prosthetic lock assembly 106.

The sealing system 103 can include at least a first seal component 107. The first seal component 107 can comprise a distal seal 108 positioned at or near the distal end 124 of the prosthetic liner 104 and configured to create a first seal around the mechanical lock between the socket 102 and the prosthetic liner 104. For instance, this first seal can seal off the prosthetic lock assembly 106, including the attachment pin 130 extending through the pin bore 120 in the socket 102, thus preventing air from entering or exiting the socket cavity 114 via the pin bore 120.

The sealing system 103 can include a second seal component 141. The second seal component 141 can be associated with the prosthetic liner 104 and/or the socket 102 and is arranged to create a second seal between the prosthetic liner 104 and the socket 102 that is located proximal to the first seal. The second seal component 141 can be at any location along a length of the prosthetic liner 104 and may be configured and positioned at a position to create an attachment area or attachment length L over which a vacuum lock is effective to retain the prosthetic liner 104 within the socket 102. For instance, the second seal component 141 can be located about halfway between the proximal and distal ends 124 of the prosthetic liner 104. The second seal component 141 can include one or a plurality of seals and can comprise a hypobaric seal, a membrane, or any other suitable seal component.

In other embodiments, the second seal component 141 can be compatible with prosthetic sleeves. The second seal component 141 can comprise an adjustable seal component. In an embodiment, the location of the second seal component 141 can be adjustable along the length of the prosthetic liner 104. The second seal component 141 can be formed on the prosthetic liner 104. Other examples of suitable seal components are found in U.S. Pat. Nos. 8,308,817; 8,097,043; 8,052,760; 8,034,120; 8,372,159; 8,372,159; 8,894,719; 8,956,422; 8,911,506; 9,056,022; 9,072,611; 9,060,885; 9,066,821; 9,295,567; 9,566,175; and 9,707,106, each of which is incorporated herein by reference in its entirety.

A sealed volume or suspension region A is defined between the first seal component 107 and the second seal component 141, and between at least a portion of the outer surface 128 of the prosthetic liner 104 and a corresponding portion of the interior surface 112 of the socket 102, substantially isolating this area from atmosphere and the mechanical lock between the prosthetic liner 104 and the socket 102.

To permit expulsion of fluid (e.g., air) from the suspension region A, a port 132 can be defined by the socket 102 that extends through the interior surface 112 and the outer surface 110 of the socket 102. The suspension region A is fluidly connected with atmosphere external to the socket 102 via the port 132. A valve may be provided separately or integrally with the port 132. The valve can be a one-way valve that selectively permits fluid to flow from the suspension region A through the port 132 to atmosphere external to the socket 102, but not in the other direction.

According to a variation, a pump system 134 may be fluidly connected with the suspension region A. The pump system 134 can be fluidly connected with the suspension region A via a tube 136 connected to the port 132. The pump system 134 can be any suitable type of pump such as a manual or electrical pump. The pump system 134 can create an elevated vacuum environment in the suspension region A, which, in turn, provides a suction tending to retain the residual limb 118 within the socket 102.

The suspension region A provides a larger attachment area or attachment length L between the prosthetic liner 104 and the socket 102 than that provided by the attachment pin 130 alone. This has the effect of reducing the likelihood of problems that can result when the attachment pin 130 pulls on the distal end 124 of the prosthetic liner 104, such as "milking," "pistoning," and attendant problems, as well as stability and rotational issues resulting from a poor fit between the socket 102 and the prosthetic liner 104.

The larger attachment area of the suspension region A pulls or holds the socket 102 and the prosthetic liner 104 together over a larger area of the prosthetic liner 104, not just at the attachment pin 130, reducing the likelihood of pistoning and milking between the residual limb 118 and the socket 102. It also helps improve rotational control and stability of the prosthetic socket system 100 because the socket 102 and the prosthetic liner 104 are more likely to move together rather than rotate or displace relative to one another during use.

Further, if the vacuum or suction in the suspension region A is unexpectedly reduced or lost, the mechanical lock between the attachment pin 130 and the socket 102 reliably keeps the socket 102 attached to the prosthetic liner 104, preventing the socket 102 from falling off the residual limb 118 and engendering greater user confidence. For example, patients or users with shorter residual limbs are often unable to confidently use prosthetic socket systems employing vacuum suspension because of a higher risk of air channeling between the prosthetic liner and the socket. With the mechanical lock between the attachment pin 130 and the socket 102 reliably attaching the socket 102 to the residual limb 118, these users can benefit from the stability and comfort offered by the sealing system 103 without worrying about the socket 102 falling off due to air channeling, for example as occurs in some existing vacuum-only suspension systems.

Accordingly, by attaching the socket 102 to the residual limb 118 using both the attachment pin 130 and suction in the sealed volume A, the prosthetic system 100 advantageously combines the benefits and reduces the shortcomings of both suspension mechanisms. Further, users of the prosthetic system 100 can experience an increased perception of suspension and stability when compared to prior art systems including a single suspension mechanism.

As discussed, the vacuum and mechanical locks or dual suspension mechanisms of the prosthetic socket system 100 can benefit a wide range of users. For instance, below-the-knee amputees can comfortably use the prosthetic socket system 100 to enjoy the comfort and stability of vacuum suspension provided by the sealing system 103 without having to worry about their prosthesis falling off. Furthermore, higher activity users can move more confidently using the prosthetic socket system 100 in challenging situations like cycling, running, and climbing. In addition, elderly or lower activity users can comfortably and confidently use the prosthetic socket system 100 without having to worry about undesirable pistoning or about a loss of suspension while the user is sitting or kneeling.

With the dual suspension mechanisms of the prosthetic socket system 100, clinicians can offer elderly patients a safe mechanical solution to the problem of sockets falling off and at the same time the benefits of vacuum suspension. Clinicians also tend to shorten the fit of a socket on a residual limb used with a locking liner because of friction concerns associated with undesirable pistoning. With the dual suspension mechanisms of the prosthetic socket system 100, clinicians can align the residual limb length more correctly with a length of the socket 102, not shorter to compensate for pistoning because of the reduced risk of pistoning provided by the sealing system 103. This helps improve the fit and support of the socket 102.

In an embodiment, the distal seal 108 has a flexible configuration and is positioned at or near the distal end 124 of the prosthetic liner 104. The distal seal 108 extends circumferentially around the attachment pin 130 and projects downwardly from a distal portion of the outer surface 128 of the prosthetic liner 104. The distal seal 108 can include a sealing portion and a variable clearance defined between the sealing portion and the distal end 124 of the prosthetic liner 104. When the prosthetic liner 104 is inserted into the socket 102, the variable clearance and a flexibility of the distal seal 108 allow the sealing portion of the distal seal 108 to deflect and deform, bridging a seal between the distal outer surface 128 of the prosthetic liner 104 and the distal interior surface 112 of the socket 102.

The variable clearance and flexibility of the distal seal 108 helps the distal seal 108 compensate for relative movement between the socket 102 and the prosthetic liner 104 by allowing the sealing portion to better move with and exert pressure against the distal interior surface 112 of the socket 102 to improve the seal bridged between the socket 102 and the prosthetic liner 104. This seals off the attachment pin 130 extending through the pin bore 120 of the socket 102, preventing air from entering or exiting the socket cavity 114 via the pin bore 120. It also isolates the mechanical lock between the prosthetic liner 104 and the socket 102 from the socket cavity 114 extending proximal to the distal seal 108, which, in turn, allows for vacuum (passive or active) to build up between the socket 102 and the liner 104 as shown in FIG. 1. The distal seal 108 thus advantageously helps the system 100 to form both a mechanical lock and a vacuum lock between the prosthetic liner 104 and the socket 102, securing the connection between the residual limb 118 and the socket 102.

The prosthetic socket system 100 can thus beneficially provide a more reliable and stable connection between the socket 102 and the prosthetic liner 104 by combining mechanical and vacuum suspension mechanisms. Moreover, the distal seal 108 can be a separate add-on module to a locking liner and can fit different liners, providing versatility and reducing costs of implementing the prosthetic socket system 100.

FIGS. 2-4 illustrate another embodiment of a prosthetic socket system 200 including a prosthetic liner 204 having an attachment pin 230, and a sealing system 203 including a first seal component 207 arranged to form a seal around the attachment pin 230, and a second seal component 241 adapted to form a second seal between the prosthetic liner 204 and a socket. Like the previous embodiment, the prosthetic liner 204 can be attached to the socket using both the attachment pin 230 and suction between the first and second seals, the prosthetic liner 204, and the socket. This allows the prosthetic socket system 200 to solve problems that can result when the attachment pin 230 pulls on the distal end 224 of the prosthetic liner 204 or when the suction between the prosthetic liner 204 and the socket is lost or reduced.

The prosthetic liner 204 is configured to be donned on a residual limb and positioned in a socket. The prosthetic liner 204 includes a liner body 222 having a proximal end, which is open, and a distal end 224, which is closed, and defines an inner surface that interfaces with the skin, and an outer surface 228 opposing the inner surface. The distal end 224 may include an umbrella 240 that enables interconnection between the prosthetic liner 204 and a prosthetic device. The umbrella 240 generally includes an umbrella-shaped base and a neck that depends from the center of the base. An internally threaded central bore is formed in the neck. The liner body 222 may be formed of an elastomer and may or may not include a fabric cover.

The attachment pin 230 is threaded into the central bore of the umbrella 240 of the prosthetic liner 204 and can engage a prosthetic lock assembly arranged to couple the liner 204 and the socket together. The attachment pin 230 can define a plurality of notches and/or can be smooth.

The first seal component 207 comprises a distal seal 208 attached to the distal end 224 of the liner 204. The distal seal 208 includes a sealing portion and has a flexible configuration arranged to create the first seal between the prosthetic liner 204 and the socket. This first seal component 207 can seal off the attachment pin 230 extending through the pin bore in a socket, preventing air from entering or exiting the socket cavity via the pin bore. It also helps define a sealed volume between the prosthetic liner 204 and the socket that isolates the mechanical lock between the prosthetic liner 204 from the socket's interior proximal to the distal seal 208, which, in turn, allows for vacuum or suction to build up between the distal seal 208, the second seal component 241, the prosthetic liner 204 and the socket.

The second seal component 241 comprises a movable seal component removably positionable on the prosthetic liner 204. The second seal component 241 includes open upper and lower ends defining an opening therethrough and an inner surface arranged to abut the outer surface 228 of the prosthetic liner 204. In an embodiment, the second seal component 241 can frictionally engage at least one of a plurality of seal bands 238 on the liner body 222 and secure on the outer surface 228 of the liner body 222. Similar to the previously described seal components, the second seal component 241 is adapted to create a second seal between the prosthetic liner 204 and a socket that is located proximal to the distal or first seal formed by the distal seal 208.

The sealing system 203 thus advantageously enables the prosthetic system 200 to form both a mechanical lock and a vacuum lock between the prosthetic liner 204 and a socket, providing reliable and comfortable prosthetic suspension and minimizing the disadvantages of existing single-lock systems.

In the illustrated embodiment, the distal seal 208 includes a base 242 and a sealing portion 256. The distal seal 208 can be attached to the distal end 224 of the prosthetic liner 204 by being secured between the umbrella 240 and the attachment pin 230. For instance, the base 242 defines a neck or stem 244 that extends from a central portion of the base 242. The base 242 can comprise a disc, a conical member, or umbrella-shaped portion adapted to interface with and fit against the umbrella 240. The base 242 can be proximate to the attachment pin 230. An opening 246 is formed in the stem 244 for engagement with the attachment pin 230. A diameter of the opening 246 can generally correspond to the diameter of the attachment pin 230. The distal seal 208 may be made of an air-impermeable material such as an elastomer material, silicone, polyurethane, or any other suitable material.

A rigid part 248 such as a washer member is associated with the stem 244. The rigid part 248 can include a support base 252 defining a central opening and annular wall 254 surrounding the support base 252. The annular wall 254 may extend either partially or entirely around an outer peripheral portion of the support base 252. In use, the rigid part 248 transfers forces between the attachment pin 230 and the umbrella 240 and away from the more flexible sealing portion 256 of the distal seal 208. The rigid part 248 may be integrally formed with the stem 244 or separate from the stem 244. For instance, at least the annular wall 254 can extend within the stem 244 of the distal seal 208. The rigid part 248 may be formed of any suitable material, including, but not limited to, thermoplastic, polyoxymethylene (POM), metal, and/or plastic.

To attach the distal seal 208 to the distal end 224 of the prosthetic liner 204, the distal seal 208 can be positioned on the umbrella 240 so that the top of the base 242 interfaces with the distal end 224 of the liner 204. A threaded proximal end of the attachment pin 230 is then passed though the opening 246 of the stem 244 and screwed into the central bore of the umbrella 240. The attachment pin 230 is screwed into the central bore of the umbrella 240 until a flange 250 defined on the attachment pin 230 engages with the rigid part 248 of the distal seal 208, which, in turn, secures or fastens the distal seal 208 between the umbrella 240 and the attachment pin 230. An outer diameter of the flange 250 can be greater than the central opening defined in the base of the rigid part 248.

To remove the distal seal 208 from the prosthetic liner 204, the attachment pin 230 can be unscrewed from the central bore of the umbrella 240 and the distal seal 208 can be pulled off the umbrella 240 and the attachment pin 230. The distal seal 208 can thus be quickly and efficiently installed, removed, and reconfigured with great ease. The distal seal 208 can be easily removed for cleaning or to be exchanged with a replacement or another distal seal adapted for a different application. Further, the distal seal 208 can be used with or retrofitted onto conventional or existing locking liners and sockets without permanent modification of their structure.

The wall segment 258 has an outer wall 259 forming an outer peripheral portion of the wall segment 258 and directed distally toward the liner body axis C with a diameter decreasing distally. The wall segment 258 defines an inner wall 261 with a conical configuration with a decreasing diameter extending toward its distal end about the liner body axis C. The outer wall 259 and the inner wall 261 secure at a maximum diameter of the inner wall 261 and a proximally-most location of the inner wall 261 at a connection point 263. The outer wall 259 and the inner wall 261 are arranged at different angles relative to one another such that a variable clearance 260 is defined between the outer wall 259 and the inner wall 261. The variable clearance 260 increases in a distal direction relative to the liner body axis C.

The variable clearance 260 is defined between the sealing portion 256 and the prosthetic liner 204 and/or base 242. In use, a residual limb is placed within the prosthetic liner 204 and both the residual limb and prosthetic liner 204 are inserted within a socket so that the distal seal 208 engages a distal interior surface of the socket. As the sealing portion 256 engages the distal interior surface of the socket, a flexibility of the distal seal 208 allows the sealing portion 256 to deflect toward the prosthetic liner 204 and deform, forming a seal between the prosthetic liner 204 and the socket. This beneficially seals around the mechanical lock effected by the attachment pin 230 between the prosthetic liner 204 and the socket, and consequently allows for a vacuum (passive or active) to be generated between the distal seal 208 and the second seal component 241. The variable clearance 260 and flexibility of the distal seal 208 helps the distal seal 208 compensate for relative movement between the socket and the prosthetic liner 204 by allowing the sealing portion 256 to better or more freely move with and exert pressure against the interior surface of the socket to improve the seal. The wall segment 258 can have an elongate configuration, increasing the surface area and consequently the effectiveness of the interface between the sealing portion 256 and the interior surface of the socket.

When a higher pressure exists on the inner side of the sealing portion 256 as compared to the outer side thereof (such as when a vacuum is created between the socket and the prosthetic liner 204), the distal seal 208 will tend to expand outwardly against the interior surface of the socket and a sealing force exerted by the distal seal 208 can increase commensurately with the pressure differential. In an embodiment, a reinforcement member or the material properties of the distal seal 208 can bias or urge the wall segment 258 away from the base 242. This advantageously increases the sealing forces between the distal seal 208 and the interior surface of the socket, improving the connection between the prosthetic liner 204 and the socket. It will also be apparent that because the distal seal 208 is located between the distal end of the liner 204 and the distal interior surface of a socket, loading from the residual limb increases the sealing forces between the sealing portion 256 and the socket.

Optionally, the distal seal 208 can include a plurality of blades 262 located along the inner surface of the sealing portion 256 and extending between the sealing portion 256 and the base 242. The blades 262 can be arranged obliquely to an axis C and arranged to collapse against the base 242 when loaded. The blades 262 may reinforce the distal seal 208 to provide a stronger interface between an interior socket wall and the prosthetic liner 204. The blades 262 can also increase the interface between the wall segment 258 and the base 242. The blades 262 can help compensate for volume changes in the residual limb by expanding and exerting pressure against an interior surface of a socket to improve the seal around the mechanical lock effected at the attachment pin 230.

The oblique orientation of the blades 262 relative to the axis C permit the blades 262 to fold toward the base 242 with the possibility of some overlap over each of the blades 262 as the distal seal 208 engages the interior socket wall. The blades 262 are at an angle to ensure that each blade folds in a proper predetermined direction to avoid the creation of pressure points. The blades 262 are not limited to an obliquely extending configuration but may be arranged in any number of configurations such as either generally parallel or perpendicular to the axis C.

Figure 5:
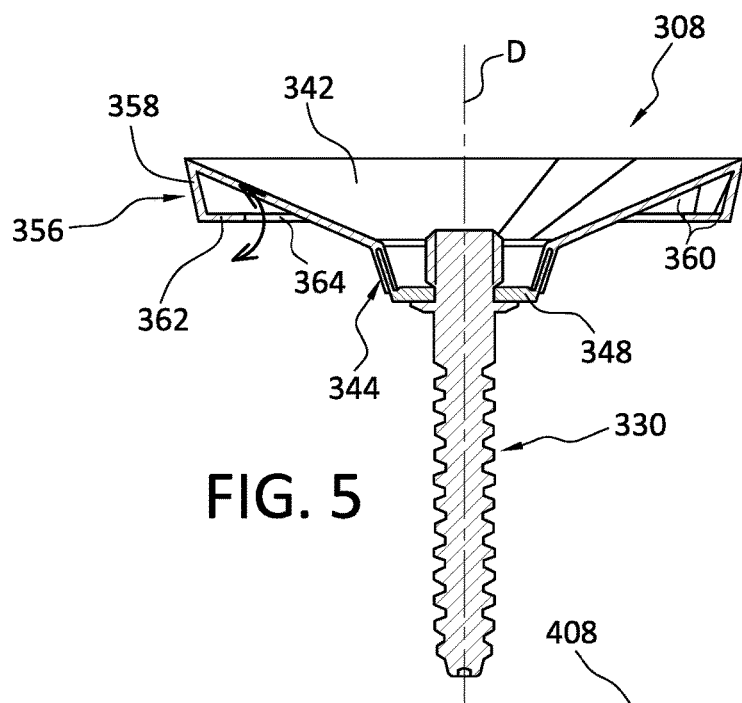
FIG. 5 shows a cross section in an elevational view of a distal seal according to another embodiment.

FIG. 5 illustrates another embodiment of a distal seal 308 of the present disclosure. The distal seal 308 can be like the distal seal 208 of the previous embodiments, having a flexible configuration and extending circumferentially about the attachment pin 330. The distal seal 308 includes a base 342 and a sealing portion 356. The base 342 can comprise a disc or conical member arranged to engage with the distal end or umbrella of a prosthetic liner. The base 342 can be proximate to the attachment pin 330.

A variable clearance 360 is defined between the sealing portion 356 and the distal end of a prosthetic liner and/or the base 342. Due to the variable clearance 360 and the flexibility of the distal seal 308, the sealing portion 358 can deflect toward the prosthetic liner and deform when it engages the distal interior surface of the socket. The sealing portion 356 is engageable with the interior surface of the socket in a manner similar to that described previously in connection with distal seal 308, bridging or forming a seal between the socket and the prosthetic liner. That is, the form of the sealing portion 356 tends to increase sealing forces when the distal seal 308 is exposed to a pressure differential between the inner and outer sides of the sealing portion 356, with the higher pressure existing towards the inner or distal side of the sealing portion 356 by pressing the sealing portion 356 into engagement with the distal interior surface of the socket. Moreover, the variable clearance 360 and the flexibility of the distal seal 308 helps the distal seal 308 compensate for relative movement between the distal interior surface of the socket and the prosthetic liner by allowing the sealing portion 356 to better move with and exert pressure against the distal interior surface of the socket to improve and maintain the seal, through a variety of user activities.

In the illustrated embodiment, the sealing portion 356 comprises a wall segment 358 extending downwardly from an outer portion of the base 342, and a lower segment 362 that extends radially inward from a distal end portion of the wall segment 358. The lower segment 362 includes a first end connected to the distal end portion of the wall segment 358 and a free end defining an opening 364. The wall segment 358 and the base 342 are sized such that the base 342 projects below or distal to the opening 364.

As seen, the wall segment 358 can be generally upright or slightly angled relative to an axis D defined by the distal seal 308 and the lower segment 362 can be generally perpendicular to the axis D. The radial orientation of the lower segment 362 increases the sealing forces between the sealing portion 356 and the interior surface of the socket, improving the seal. The transecting orientations of the wall segment 358 and the lower segments 362 also assist the distal seal 308 in maintaining its shape as the distal seal 308 flattens when donned and pressed against the socket. Similar to the distal seal 208, the base 342 defines a stem 344 that extends from a central portion of the base 342 and defines an opening for engagement with an attachment pin 330, and a rigid part 348.

Figure 7:
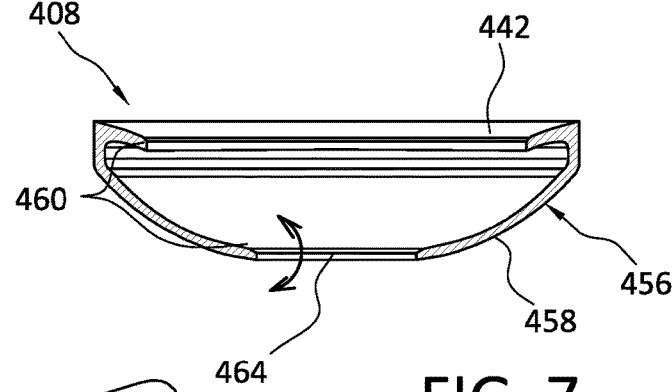
FIG. 7 shows a cross section of the distal seal of FIG. 6 in an elevational view.
Figure 6:
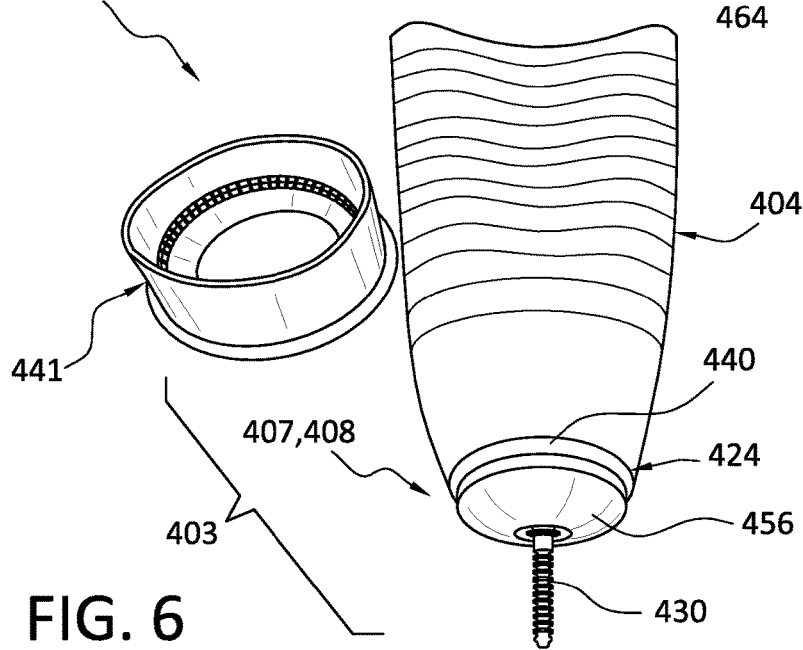
FIG. 6 shows a perspective view of a prosthetic socket system according to another embodiment.

FIGS. 6 and 7 illustrate yet another embodiment of a prosthetic socket system 400 including a prosthetic liner 404 having an attachment pin 430, a sealing system 403 comprising a first seal component 407 adapted to form a first seal around the mechanical lock of the prosthetic socket system 400 and a second seal component 441 adapted to from a second seal between the prosthetic liner 404 and a socket, the second seal being located proximal to the first seal. Like the previous embodiment, the prosthetic liner 404 is thus attachable to a socket using both the attachment pin 430 and a vacuum lock or suction in a suspension region defined between first and second seals, the prosthetic liner 404, and the socket. This allows the prosthetic socket system 400 to provide a more secure and stable attachment between the prosthetic liner 404 and the socket than in prior art systems, improving user confidence and comfort.

The first seal component 407 comprises a distal seal 408 having a flexible configuration. The distal seal 408 includes a base 442 attachable to the prosthetic liner 404 and a sealing portion 456 comprising a wall segment 458. The base 442 can comprise a disc or conical member arranged to engage a distal end 424 and/or an umbrella 440 of the prosthetic liner 404. The base 442 can be configured to be proximate to the attachment pin 430.

A variable clearance 460 is defined between the sealing portion 456 and the base 442. Due to the variable clearance 460 and a flexibility of the distal seal 408, the sealing portion 456 can deflect toward a distal end 424 of the prosthetic liner 404 and/or the base 442 and deform when it engages the distal interior surface of a socket, forming the first seal between the prosthetic liner 404 and the socket. This beneficially seals around the attachment pin 430, and consequently allows for vacuum to be generated between the first seal formed by the distal seal 408 and the second seal formed by the second seal component 441. The variable clearance 460 and flexibility of the distal seal 408 help the distal seal 408 compensate for relative movement between the distal interior surface of the socket and the prosthetic liner 404 by allowing the sealing portion 456 to better move with and exert pressure against the distal interior surface of the socket to improve the first seal. Thus the vacuum does not fail when a user engages in various activities or as the mechanical attachment shifts, which shifting is minimized by the vacuum.

The sealing portion 456 extends downwardly from the base 442 and has an outer curvature descending to a central opening 464 sized to allow the attachment pin 430 to pass therethrough. A diameter of the central opening 464 substantially corresponds to a diameter of the attachment pin 430. As such, the sealing portion 456 is defined along almost the entire outer surface of the distal seal 408, generally covering the distal end 424 and/or an umbrella 440 on the distal end 424 and increasing the sealing contact area between the distal seal 408 and a socket. As seen, an inner diameter of the base 442 is greater than the diameter of the central opening 464.

The curved form of the sealing portion 456 advantageously can decrease the likelihood of the distal seal 408 undesirably sticking to or flattening out against the base 442 when the distal seal 408 is inserted into a socket. It also provides an increased sealing force between the distal seal 408 and a socket.

The base 442 can comprise a disc or conical ring adapted to interface with and fit against the distal end 424 of the liner 404. The base 442 is preferably attachable to the distal end 424 of the prosthetic liner 404 via an adhesive such that it can be quickly and efficiently installed on the prosthetic liner 404. For instance, the base 442 can be glued to the distal end 424 of the prosthetic liner 404, forming a sealing point or sealing area between the distal seal 408 and the prosthetic liner 404. Moreover, the distal seal 408 can be a separate add-on module to the prosthetic liner 404 and can fit different liners, providing versatility. Thus existing or conventional liners may be easily adapted or retrofitted for use with the prosthetic socket system 400 of the disclosure.

Figure 8:
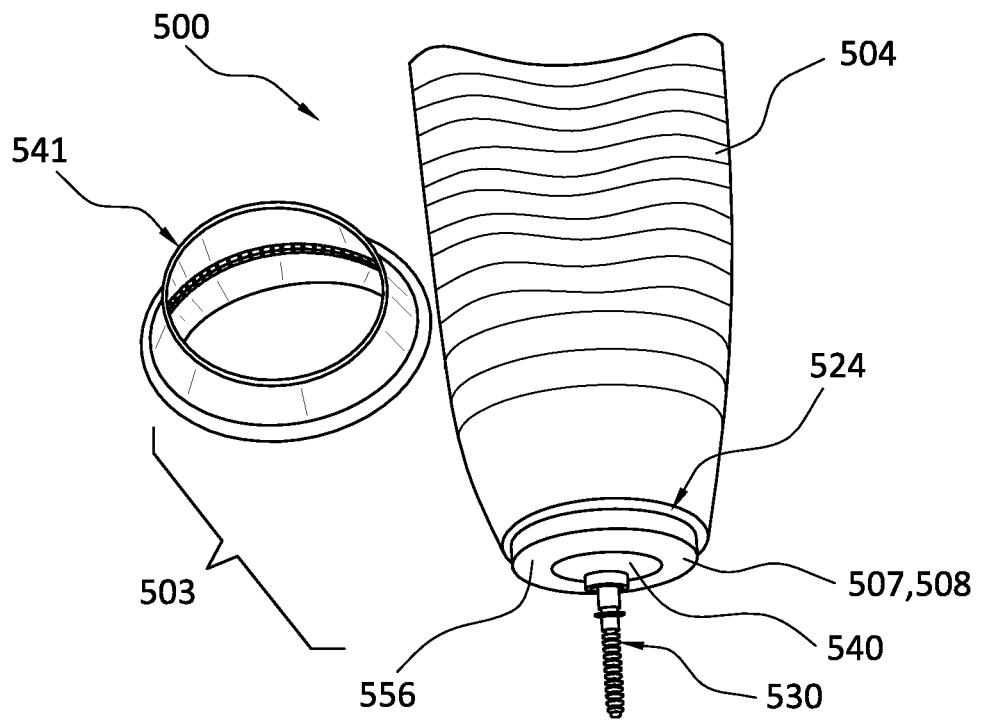
FIG. 8 shows a perspective view of a prosthetic socket system according to another embodiment.
Figure 9:
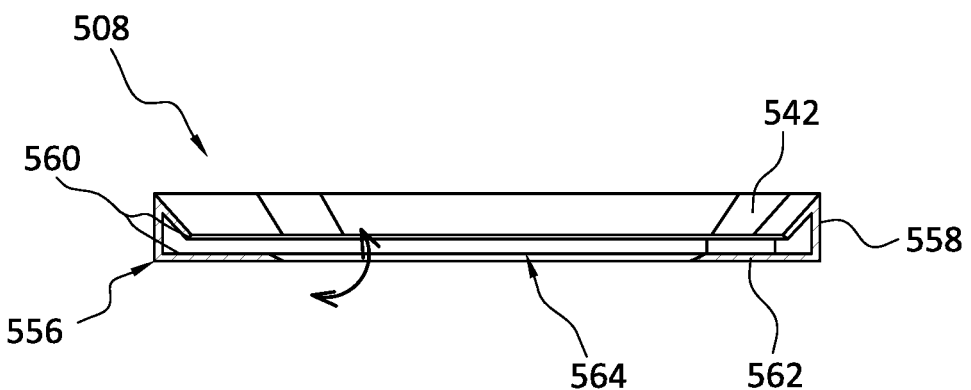
FIG. 9 shows a cross section of the distal seal of FIG. 8 in an elevational view.

FIGS. 8 and 9 illustrate yet another embodiment of a prosthetic system 500 including a prosthetic liner 504 having an attachment pin 530, and a sealing system 503 comprising a first seal component 507 arranged to form a first seal around a mechanical lock between the attachment pin 530 and a socket, and a second seal component 541 arranged to form a second seal between the prosthetic liner 504 and the socket, the second seal being proximal to the first seal. This allows the prosthetic liner 504 to attach to the socket using both a mechanical lock with the attachment pin 530 and elevated vacuum or suction in a sealed or substantially sealed region defined between the first and second seals, the prosthetic liner 504, and the socket.

The first sealing component 507 can comprise a distal seal 508 having a flexible configuration and including a base 542 attachable to the prosthetic liner 504, and a sealing portion 556. A variable clearance 560 is defined between the sealing portion 556 and the prosthetic liner 504 and/or the base 542. Due to the variable clearance 560 and a flexibility of the distal seal 508, the sealing portion 556 can deflect toward the prosthetic liner 504 and/or the base 542 and deform when it engages the distal interior surface of a socket, forming the first seal between the prosthetic liner 504 and the socket. This beneficially seals around the mechanical lock between the attachment pin 530 and the socket, separating the area proximate the mechanical lock and consequently allows for vacuum to be generated between the distal seal 508 and the first seal element 541. The variable clearance 560 and the flexibility of the distal seal 508 helps the distal seal 508 compensate for relative movement between the distal interior surface of the socket and the prosthetic liner 504 by allowing the sealing portion 556 to better move with, comfort to, and exert pressure against the distal interior surface of the socket to improve the seal.

The sealing portion 556 comprises a wall segment 558 extending downwardly from an outer portion of the base 542, and a lower segment 562 that extends radially inward from a distal end portion of the wall segment 558. The lower segment 562 includes a first end connected to the distal end portion of the wall segment 558 and a free end defining an opening 564. The wall segment 558 and the base 542 are sized such that the base 542 terminates above the opening 564, lowering the overall profile of the distal seal 508. The lower segment 562 and opening 564 are sized so that an umbrella 540 of the prosthetic liner 504 projects below the distal seal 508 and the attachment pin 530 exits the umbrella 540 below the distal seal 508.

Referring again to the base 542, it can comprise a conical ring adapted to interface with and fit against a distal end 524 of the prosthetic liner 504. The base 542 can be proximate to the attachment pin 530. The base 542 is preferably attachable to the distal end 524 and/or an umbrella 540 on the distal end 524 via an adhesive such that it can be quickly and efficiently installed on the prosthetic liner 504. Moreover, like other embodiments, the distal seal 508 can be a separate add-on module to the prosthetic liner 504 and can fit different liners, providing versatility.

Figure 10:
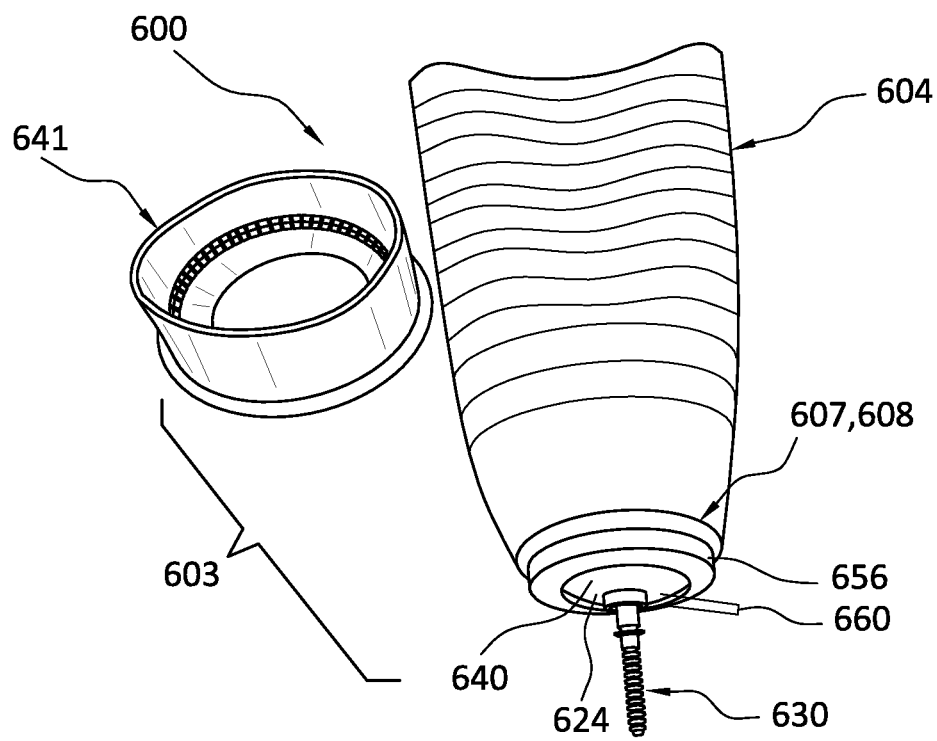
FIG. 10 shows a perspective view of a prosthetic socket system according to another embodiment.
Figure 11:
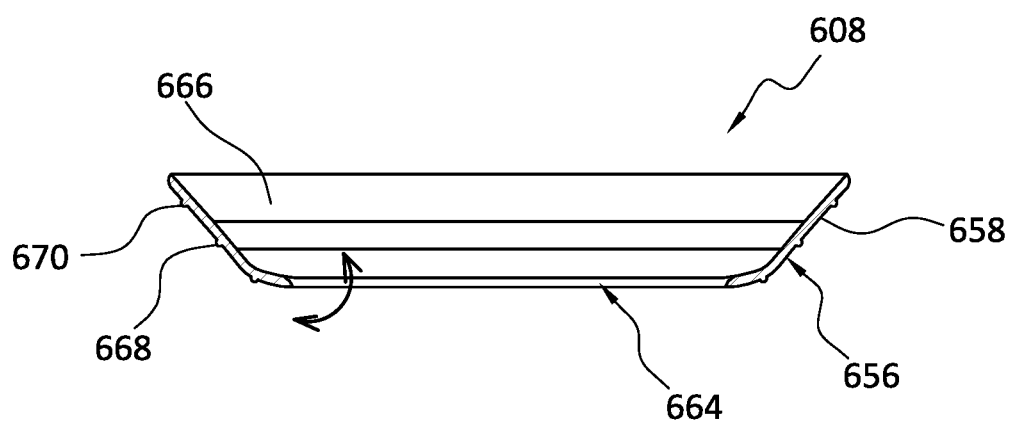
FIG. 11 shows a cross section of the distal seal of FIG. 10 in an elevational view.
Figure 12:
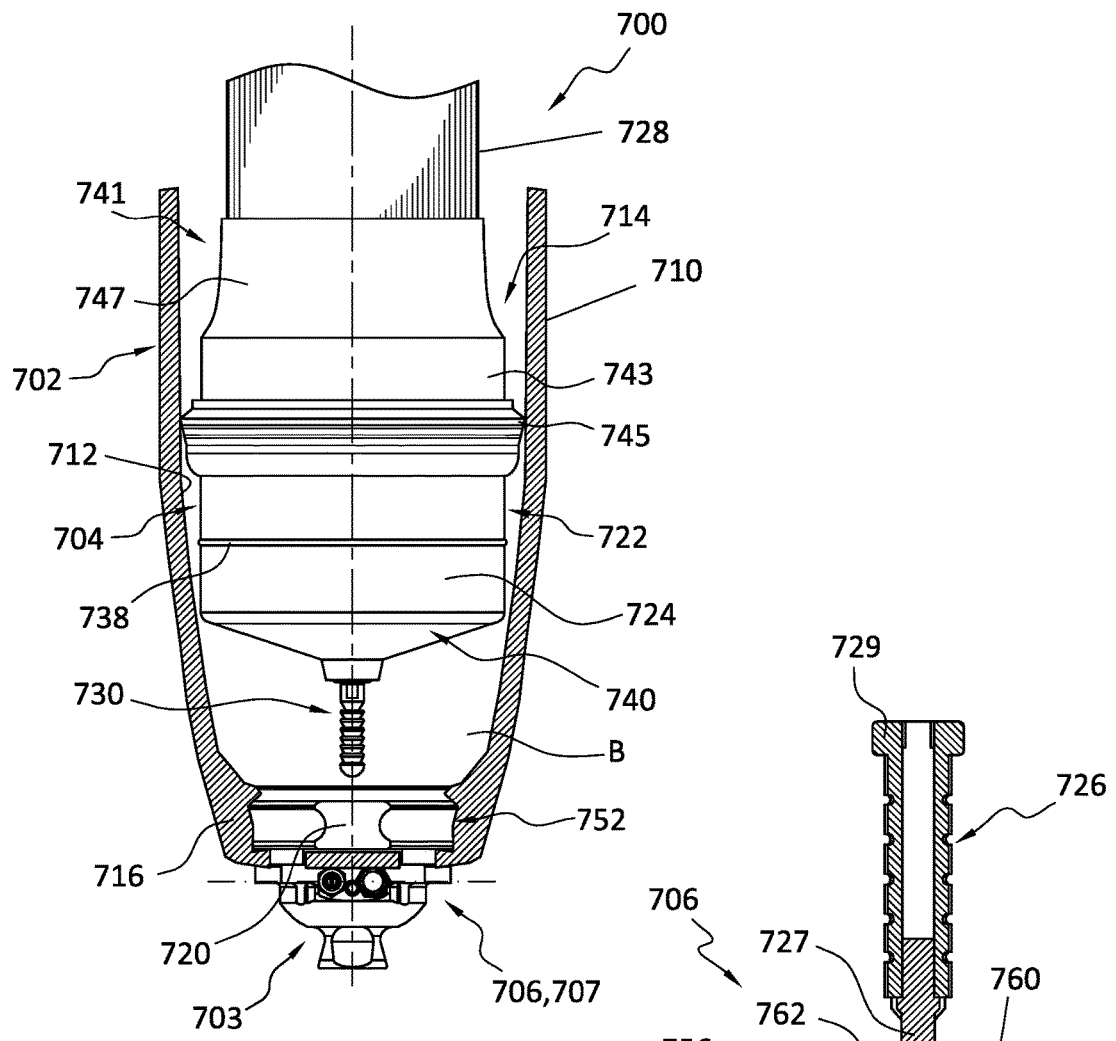
FIG. 12 shows a partial cross section in an elevational view of a prosthetic socket system according to another embodiment.

FIGS. 10 and 11 illustrate yet another embodiment of a prosthetic system 600 including a prosthetic liner 604 having an attachment pin 630, and a sealing system 603 comprising a first seal component 607 arranged to form a first seal around a mechanical lock between the attachment pin 630 and a socket, and a second seal component 641 arranged to form a second seal between the prosthetic liner 604 and the socket. The prosthetic liner 604 is attachable to the socket using both the attachment pin 630 and elevated vacuum or suction in a sealed or substantially sealed region defined between the first and second seals, the prosthetic liner 604, and the socket.

The first seal component 607 can comprise a distal seal 608 having a flexible configuration and extending circumferentially around the attachment pin 630 and including a sealing portion 656 comprising a wall segment 658. A variable clearance 660 is defined between the sealing portion 656 and a distal end 624 of the liner 604. Due to the variable clearance 660 and a flexibility of the distal seal 608, the sealing portion 656 can deflect toward the distal end 624 and/or an umbrella 640 on the distal end 624 and deform when it engages the distal interior surface of a socket, such as when a residual limb is inserted, forming the first seal between the prosthetic liner 604 and the socket. This advantageously seals around the mechanical lock including the attachment pin 630, and consequently allows for vacuum to be generated between the first seal formed by the distal seal 608 and the second seal formed by the second seal component 641, without affecting the strength or operation of the mechanical lock. The variable clearance 660 and the flexibility of the distal seal 608 helps the distal seal 608 compensate for relative movement between the distal interior surface of the socket and the prosthetic liner 604 by allowing the sealing portion 656 to better move with and exert pressure against the distal interior surface of the socket to improve and maintain the seal during movements by a user.

A proximal inner surface 666 of the sealing portion 656 is adapted to interface with and fit against the distal end 624 of the prosthetic liner 604. In an embodiment, the proximal inner surface 666 is attachable to the distal end 624 and/or the umbrella 640 via an adhesive such that it can be quickly and efficiently installed on the prosthetic liner 604. As such, the sealing portion 656 can both form a seal between the prosthetic liner 604 and a socket and connect the distal seal 608 to the prosthetic liner 604. Moreover, the distal seal 608 can be a separate add-on module to the prosthetic liner 604 and can fit different liners, improving versatility, convenience, and affordability.

In an embodiment, the sealing portion 656 extends downwardly from its attachment to the umbrella 640 and has a conical and/or an outer shape or curvature descending to a central opening 664 sized to allow the umbrella 640 and attachment pin 630 to protrude through the central opening 664. A diameter of the opening 664 is greater than the diameter of the attachment pin 630 and smaller than the outer diameter of the umbrella 640.

The sealing portion 656 includes at least one radial seal 668, 670, and preferably at least two radial seals projecting outwardly from the wall segment 658. The radial seals are arranged to help maintain connection with the interior surface of a socket, improving the reliability of the seal formed by the distal seal 608.

FIGS. 12-17 illustrate a prosthetic socket system 700 according to yet another embodiment of the present disclosure. The prosthetic socket system 700 includes a socket 702, a prosthetic liner 704, and a prosthetic lock assembly 706. The socket 702 has an outer surface 710 and an opposing interior surface 712 defining a socket cavity 714. The socket cavity 714 includes an open proximal end and a distal end 716. The open proximal end is adapted to receive a distal end of a residual limb inserted in the socket cavity 714. The distal end 716 defines a pin bore 720 extending therethrough.

The prosthetic liner 704 is configured to be donned on the residual limb and positioned in the socket cavity 714. The prosthetic liner 704 includes a liner body 722 having a proximal end, which is open, and a distal end 724, which is closed. The liner body 722 defines an inner surface that interfaces with the skin, and an outer surface 728 opposing the inner surface. The outer surface 728 includes a plurality of seal bands 738. The liner body 722 can be formed of a polymeric or elastomeric material like silicone, copolymer gel, polyurethane, combinations thereof, or the like.

An attachment pin 730 is secured to the distal end 724 of the prosthetic liner 704. In an embodiment, the attachment pin 730 is secured to the prosthetic liner 704 via an umbrella 740 connected to or integrated with the distal end 724. The attachment pin 730 is adapted to extend through the pin bore 720 of the socket 702 and thus through the distal end 716 of the socket 702. The attachment pin 730 can define a plurality of notches, threadings, or serrations 732 (shown in FIG. 14A). The attachment pin 730 can be mounted to the prosthetic liner 704 or threaded onto the distal end 724 of the prosthetic liner 704.

The prosthetic lock assembly 706 is configured to connect the residual limb, indirectly or directly, to the prosthetic socket 702. Preferably, the prosthetic lock assembly 706 includes a lock body 750 configured to attach the prosthetic lock assembly 706 to the socket 702 such that the attachment pin 730 may be inserted in an opening of the lock body 750. The prosthetic lock assembly 706 is shown including a mounting plate 752 laminated into the distal end 716 of the socket 702 but may be located above or below the distal end 716 of the socket 702. The prosthetic lock assembly 706 is configured to connect to prosthetic components and effectively couples the prosthetic liner 704, the socket 702, and other components.

When the attachment pin 730 passes through the pin bore 720 of the socket 702, the lock body 750 can receive and lock the attachment pin 730 therein, which, in turn, mechanically couples the prosthetic liner 704 to the socket 702. This mechanical lock or attachment of the prosthetic liner 704 to the socket 702 can be released via a release mechanism 726 of the prosthetic lock assembly 706. The engagement between the attachment pin 730 and the prosthetic lock assembly 706 thus mechanically locks or couples the distal end 724 of the prosthetic liner 704 to the distal end 716 of the socket 702, providing a user with safe and reliable suspension.

In addition to the mechanical lock between the prosthetic liner 704 and the distal end 716 of the socket 702, the prosthetic socket system 700 can include a sealing system 703 configured to allow an elevated vacuum or vacuum lock to be generated between the prosthetic liner 704 and the socket 702 for vacuum suspension.

The sealing system 703 can include at least a first seal component 707. The first seal component 707 can comprise the prosthetic lock assembly 706 configured to create both the mechanical lock between the socket 702 and the prosthetic liner 704, and a first seal isolating the mechanical lock and/or the pin bore 720 from atmosphere.

The sealing system 703 can also include a second seal component 741. The second seal component 741 can be a movable seal component removably positioned on the prosthetic liner 704. The second seal component 741 includes a body 743 having open upper and lower ends defining an opening therethrough and an inner surface arranged to abut the outer surface 728 of the prosthetic liner 704. The second seal component 741 includes at least one seal element 745 arranged to engage with the interior surface 712 of the socket 702 and form the second seal between the prosthetic liner 704 and the socket 702.

The second seal component 741 can frictionally engage at least one of the seal bands 738 on the liner body 722 and secure on the outer surface 728 of the liner body 722. The second seal component 741 can be selectively positioned on the liner body 722 based on a shape of the residual limb. In other embodiments, the second seal component 741 can be moved around on the liner body 722 within a day or period of activity for relief and/or user comfort.

Optionally, a sleeve 747 having a tubular form is secured to the open upper end of the second seal component 741. The sleeve 747 can have a different elasticity from the second seal component 741. For instance, the sleeve 747 can be formed from a textile and the second seal component 741 can be formed from a polymeric material, such as an injection-molded silicone to form the definitive shape of the second seal component 741. The sleeve 747 is preferably configured and dimensioned to securely tension over the prosthetic liner 704.

A sealed volume or suspension region B is defined between the first seal element 707 and the second seal element 741, and between at least a portion of the outer surface 728 of the prosthetic liner 704 and a corresponding portion of the interior surface 712 of the socket 702, substantially isolating this area from atmosphere. According to a variation, a pump system may be fluidly connected with the suspension region B. The pump system can be a manual or electrical pump and can create an elevated vacuum environment in the suspension region B, which, in turn, provides a vacuum lock or suction tending to retain a residual limb within the socket 702.

The suspension region B provides a larger attachment area or attachment length between the prosthetic liner 704 and the socket 702 than that provided by the attachment pin 730 alone. This reduces the likelihood of problems that can result when the attachment pin 730 pulls on the distal end 724 of the prosthetic liner 704. For instance, the larger attachment area of the suspension region B reduces the likelihood of "pistoning" and "milking" between the residual limb and the socket 702. It also helps improve rotational control and stability of the prosthetic socket system 700 because the socket 702 and the prosthetic liner 704 are more likely to move together rather than rotate or displace relative to one another during use of the prosthetic socket system 700.

Further, if the vacuum lock or suction in the suspension region B is unexpectedly reduced or lost, the mechanical lock between the attachment pin 730 and the socket 702 reliably keeps the socket 702 attached to the prosthetic liner 704, preventing the socket 702 from falling of the residual limb and thereby preventing possible injury. As in previous embodiments, the combination of the mechanical and vacuum lock systems in the prosthetic socket system 700 provides the individual benefits of each system while minimizing the corresponding drawbacks, providing numerous benefits for users of particular dimensions and conducting different activities, and further enhances comfort and compliant use.

Figure 13:
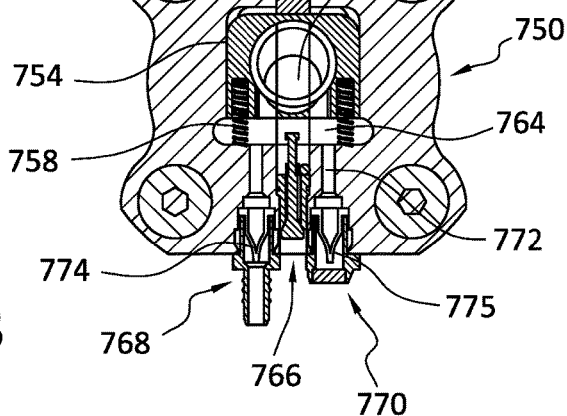
FIG. 13 shows a cross section in a plan view of the prosthetic lock assembly of FIG. 12.

The prosthetic lock assembly 706 comprising the first seal component 707 is described in additional detail with reference to FIGS. 13-17. As seen, the prosthetic lock assembly 706 includes the lock body 750 adapted to attach to the distal end 716 of the socket 702. Referring to FIG. 13, the lock body 750 can be attached to the distal end 716 of the socket 702 via one or more fasteners 756 extending through fastener holes defined in the lock body 750 and threadedly attached to the lamination member 752 mounted in the distal end of the socket 702. The lock body 750 can be made of any suitable material. The material selection can depend on desired function. The lock body 750 can be formed of stainless steel, enhancing the durability and stability of the lock body 750. The lock body 750 can include a stiff plastic material, a stiff elastomeric material, a metal material, or any other suitable material.

The lock body 750 defines a pin hole 760 for receiving the attachment pin 730, a radial bore 762 intersecting the pin hole 760, and a chamber 764 carrying a locking device 754 that selectively locks on the attachment pin 730 and fluidly connects the pin hole 760 and the radial bore 762. The lock body 750 includes an integrated prosthetic adaptor 751 defining an internal space 749 having a closed bottom configured and sized to accommodate the attachment pin 730 when the attachment pin 730 is inserted in the prosthetic lock assembly 706. Because the adaptor 751 is integrated with lock body 750, the build height and weight of the prosthetic lock assembly 706 can be reduced. The internal space 749 can form a lower area of the pin hole 760.

Moreover, the closed distal end of the lock body 750 can help assist a user with donning the prosthetic socket system 700. For instance, engagement between the closed distal end of the lock body 750 and an end of the attachment pin 730 can provide feedback to a user that the attachment pin 730 is fully inserted in the prosthetic lock assembly 706, assisting with donning the prosthetic socket system 700. In other embodiments, the internal space 749 defined by the lock body 750 can have an open bottom. For instance, the attachment pin 730 can pass through a pressed sealing ring carried in the lock body 750 that seals against the attachment pin 730 and separates the chamber 764 from atmosphere.

A locking device 754 is arranged to unidirectionally and selectively lock the attachment pin 730 in the lock body 750 while permitting insertion of the attachment pin 730 in the lock body 750. The locking device 754 also actuates a valve assembly described below, the valve assembly arranged to allow air or other fluid to enter the lock body 750 and the suspension region B. The locking device 754 can have any suitable shape and defines a through hole allowing the attachment pin 730 to pass therethrough. The through hole can be oversized relative to a diameter of the attachment pin 730 such that the locking device 754 can translate back and forth relative to the attachment pin 730 when the attachment pin 730 is inserted in the through hole.

Figure 14A:
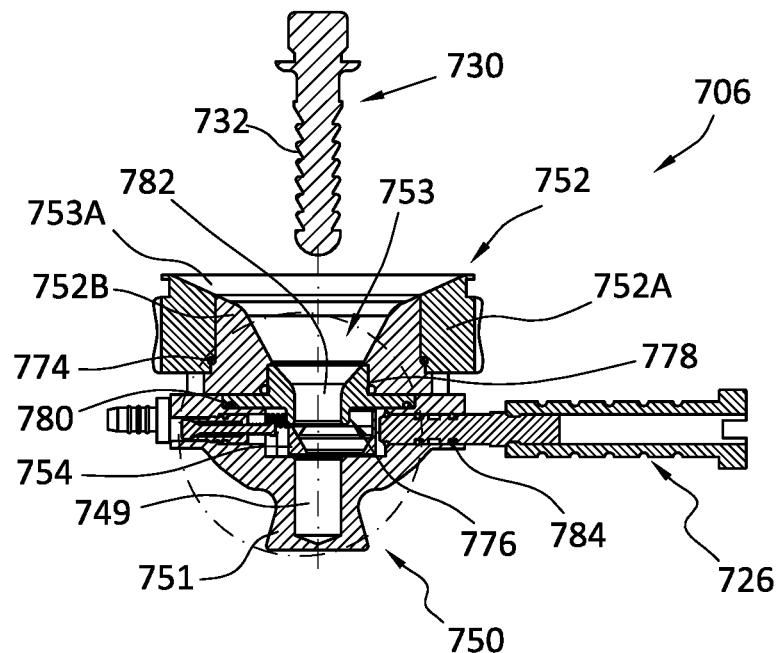
FIG. 14A shows a cross section in an elevational view of the prosthetic lock assembly of FIG. 12 in a first position.
Figure 14B:
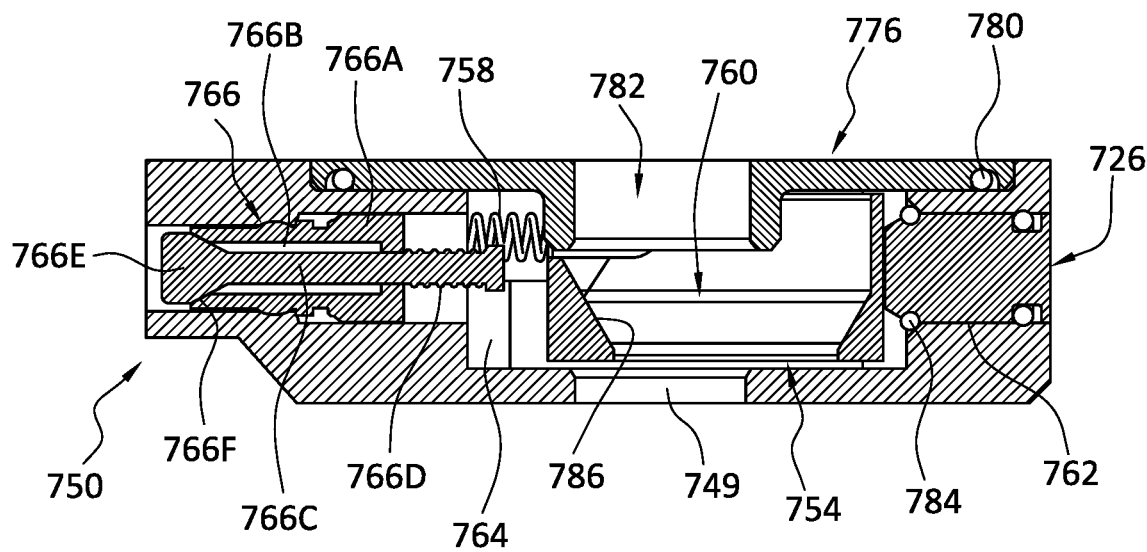
FIG. 14B shows a detail view of the cross section of the prosthetic lock assembly of FIG. 14A.

As seen in FIG. 14B, the locking device 754 defines a pin engagement part 786 configured to unidirectionally lock the attachment pin 730 in the lock body 750 while permitting insertion of the attachment pin 730 in the lock body 750. More particularly, the pin engagement part 786 is configured such that as the attachment pin 730 moves through the pin hole 760, sliding contact between the pin engagement part 786 and the attachment pin 730 moves the locking device 754 within the chamber 764 and permits insertion of the attachment pin 730 in the pin hole 760. Interaction between the pin engagement part 786 and the attachment pin 730 in the pin hole 760 can also unidirectionally lock the attachment pin 730 in the lock body 750.

For instance, when the pin engagement part 786 is captured between adjacent serrations 732 of the attachment pin 730, the pin engagement part 786 can unidirectionally lock the attachment pin 730 in the lock body 750. A release mechanism 726 is positioned in the radial bore 762 on a side of the locking device 754 opposite of a valve assembly 766 described below. The release mechanism 726 is manually operable to disengage the locking device 754 from the attachment pin 730 and to operate the valve assembly 766.

The locking device 754 is shown comprising a shuttle lock but can comprise any suitable locking device. For instance, the locking device 754 can comprise a ratchet type lock having a pawl member configured to engage the serrations 732 on the attachment pin 730. The release mechanism 726 can be releasably connected to the pawl member to disengage the pawl member from the attachment pin 730 and operate the valve assembly 766.

In addition to the mechanical lock, the buildup and release of vacuum between the socket 702 and the prosthetic liner 704 can be controlled through the prosthetic lock assembly 706. This beneficially eliminates the need for a separate port defined in the socket 702 and/or a separate valve to permit expulsion of fluid or air from the suspension region B, reducing the overall weight and complexity of the socket 702 especially when configuring it with a conventional or existing prosthetic socket system. As described below, the prosthetic lock assembly 706 selectively isolates the suspension region B from atmosphere and can be passive and active vacuum compatible.

To permit expulsion of fluid (e.g., air) from the suspension region B, the prosthetic lock assembly 706 can include one or more one-way valves. In an embodiment, two one-way valves 768, 770 positioned in the lock body 750 are in fluid communication with the chamber 764, which, in turn, is in fluid communication with the suspension region B via the pin bore 720 of the socket 702. In the illustrated embodiment, the one-way valves 768, 770 are located on opposite sides of the valve assembly 766. Each of the one-way valves 768, 770 preferably includes a duckbill valve 774, 775 that only allows air or other fluids to exit the chamber 764. It should be appreciated, however, that other types of one-way valves are possible.

The one-way valve 768 is configured to facilitate the buildup of an active vacuum in the suspension region B. For instance, the one-way valve 768 can be configured for connection to a pump system. When the pump system applies a vacuum to the chamber 764 via the one-way valve 768, fluid is drawn from the chamber 764 and the suspension region B, applying a vacuum in the suspension region B. Air can be evacuated from the suspension region B through the one-way valve 768 in several different ways including, but not limited to, a hand pump, an electronic pump, or a mechanical pump activated by the motion of the user walking, for example. The prosthetic lock assembly 706 is thus passive and active vacuum compatible so that a vacuum can be drawn through the prosthetic lock assembly 706 rather than through a separate port defined in the socket 702, simplifying the cost, complexity, and operation of the prosthetic socket system 700.

The one-way valve 770 can be configured as a one-way expulsion valve, only permitting fluid to be expelled out of the suspension region B and the chamber 764, preferably to atmosphere. The one-way valve 770 preferably has a low opening pressure such that the prosthetic lock assembly 706 can automatically expel air from the suspension region B while a user is donning the prosthetic socket system 700 or ambulating. The lock body 750 defines one or more internal passageways 772 providing fluid communication between the chamber 764 and the one-way valves 768, 770.

The valve assembly 766 is positioned in the lock body 750 opposite the release mechanism 726. The valve assembly 766 extends into and is fluidly connected to the chamber 764. In an embodiment, the valve assembly 766 is recessed within an opening formed in the lock body 750. The valve assembly 766 is operable to allow air or other fluid to enter the suspension region B via the valve assembly 766, releasing a vacuum in the suspension region B.

As seen, the valve assembly 766 comprises a valve body 766A defining a passageway 766B extending therethrough. The valve body 766A carries a pin member 766C and a spring member 766D. The pin member 766C defines a head portion 766E and extends from the valve body 766A so that the pin member 766C can selectively engage with the locking device 754. The passageway 766B includes an enlarged portion that defines a seat 766F for the head portion 766E of the pin member 766C. Generally, when the head portion 766E engages or contacts the seat 766F, the valve assembly 766 is in a closed position (shown in FIG. 14B). In the closed position, the head portion 766E is forced against the seat 766F by the spring 766D to prevent fluid flow through the valve assembly 766.

When the head portion 766E is disengaged from the seat 766F, the valve assembly 766 is in an open position. In the open position, the passageway 766B is unsealed and fluid communication between the suspension region B and atmosphere via the passageway 766B is established, allowing air or other fluid to enter the suspension region B. This has the effect of releasing a vacuum in the suspension region B.

The spring member 766D is adapted to bias the valve assembly 766 toward the closed position. For instance, in the closed position, the spring member 766D biases the head portion 766E toward the seat 766F of the valve body 766A, sealing the valve assembly 766 and creating a fluid separation between atmosphere and the suspension region B. When the release mechanism 726 moves the valve assembly 766 from the closed position toward the open position, the head portion 766E compresses or further compresses the spring member 766D between the head portion 766E and another component (e.g., the valve body 766A). When the load applied to the release mechanism 726 is released, stored energy in the spring member 766D can force the head portion 766E back into the seat 766F to return the valve assembly 766 to the closed position. Thus, the spring member 766D can help automatically close the valve assembly 766. The valve assembly 766 can comprise a pin valve, a needle valve, a bicycle valve, a membrane valve, a bladder, or any other suitable type of valve.

Manual operation of the release mechanism 726 translates the locking device 754 in the lock body 750 to unlock the attachment pin 730 from the lock body 750 and to move the valve assembly 766 to the open position, which, in turn, releases a vacuum in the suspension region B. The release mechanism 726 thus releases both the mechanical lock and the vacuum lock of the prosthetic socket system 700. The release mechanism 726 is preferably arranged to unlock the attachment pin 730 and vacuum in the suspension region B with a single action. This simplified operation of the release mechanism 726 is particularly advantageous for elderly or other users having limited dexterity and/or strength.

One or more spring members 758 engaging the locking device 754 in the chamber 764 are arranged to bias the locking device 754 away from the valve assembly 766. The spring members 758 can be selected such that the release mechanism 726 can be operated with a reduced force. For instance, the spring members 758 can be sized and configured such that the release mechanism 726 working against the spring members 758 can be operated with a release force less than between about 50 N and about 70 N (e.g., 60 N). A handle 729 is preferably provided on the rod 727 to assist operation thereof.

Referring to FIG. 14A, a central opening 753 is defined in the mounting plate 752 that is oversized and configured to receive the attachment pin 730. For instance, the mounting plate 752 can define the central opening 753 and includes an annular flange 753A surrounding the central opening 753 and extending axially upward and radially away from a top of the central opening 753 as shown. The annular flange 753A can help funnel or guide the attachment pin 730 into the pin hole 760. This advantageously makes donning the socket 702 easier. This annular flange 753A can also help forgive poor alignment of the prosthetic liner 704 within the socket 702. This is beneficial as the user does not have to "thread the needle," which increases the risk of incorrect attachment and injury, but rather the user is provided with an intuitive and forgiving attachment means. The annular flange 753A can define a surface arranged to interact with an umbrella 740 or the distal end 724 of the prosthetic liner 704. In an embodiment, the mounting plate 752 can include a two-part construction. For instance, the mounting plate 752 can include an outer part 752A and an inner part 752B threadedly attached to the outer part 752A. A cover member 776 is positioned under the mounting plate 752 and includes an opening 782 arranged to align the attachment pin 730 within the lock body 750.

A seal member 774 may be provided between the outer part 752A and the inner part 752B to ensure a seal therebetween. The mounting plate 752 is sealed to the cover member 776 by a sealing member 778, and the cover member 776 is sealed to the lock body 750 by a sealing member 780. The release mechanism 726 is sealed in the radial bore 762 by a plurality of sealing members 784. These sealing members may comprise O-rings and can help ensure that fluid (e.g., air) can only enter the chamber 764 via the valve assembly 766 and can only exit the chamber 764 via the one-way valves 768, 770. In an embodiment, the prosthetic lock assembly 700 has a waterproof configuration. For instance, the sealing members 778, 780, 784 in combination with the closed bottom of the lock body 750, can prevent water from entering the socket 702 via the pin bore 720, improving reliability and hygiene of the prosthetic socket system 700.

The sealing members 778, 780, 784 in combination with the closed bottom of the lock body 750, additionally help the prosthetic lock assembly 706 to work using different types of prosthetic liners. More particularly, because the prosthetic lock assembly 706 does not need a physical seal against the attachment pin 730 for a vacuum lock within the suspension region B, the vacuum lock formed by the prosthetic lock assembly 706 is independent from the presence of the attachment pin 730. The mechanical lock formed by the prosthetic lock assembly 706 with the attachment pin 730 is also independent of the vacuum lock. As such, the prosthetic lock assembly 706 does not need a prosthetic liner with an attachment pin to maintain a vacuum lock. Further, the prosthetic lock assembly 706 does not need a vacuum lock to form a mechanical lock with the attachment pin 730. The prosthetic lock assembly 706 thus offers users and clinicians great versatility in selecting a prosthetic liner.

For instance, a clinician may instruct a user to wear a locking prosthetic liner (e.g., a liner including only an attachment pin) one day using the prosthetic lock assembly 706, a suction type prosthetic liner (e.g., a liner including only a seal element) another day using the prosthetic lock assembly 706, and a suction-locking prosthetic liner (e.g., a liner including a seal element and attachment pin) yet another day using the prosthetic lock assembly 706. This dual or alternate suspension capability of the prosthetic lock assembly 706 allows the prosthetic lock assembly 706 to be used with different prosthetic liners as needed or desired, and as best suits a user's needs and activities.

In use, the prosthetic lock assembly 706 is movable between different positions and configurations for selectively controlling the mechanical and vacuum lock between the prosthetic liner 704 and the socket 702. With the attachment pin 730 separate from the lock body 750 and the release mechanism 726 unengaged, the prosthetic lock assembly 706 can be in an unlocked position as shown in FIGS. 14A and 14B. In the unlocked position, the pin engagement part 786 of the locking device 754 is at least partially located in the pin hole 760 between the internal space 749 of the lock body 750 and the central opening 753. This ensures that the attachment pin 730 will engage the pin engagement part 786 of the locking device 754 as it passes through the pin hole 760. The locking device 754 can be engaged with the release mechanism 726 and disengaged from the valve assembly 766.

Figure 15A:
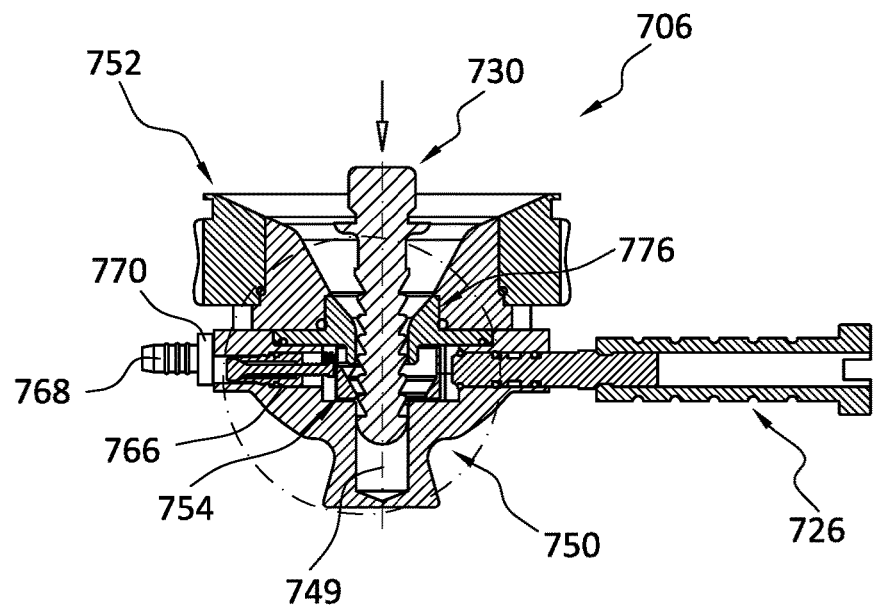
FIG. 15A shows a cross section in an elevational view of the prosthetic lock assembly of FIG. 12 in a second position.
Figure 15B:
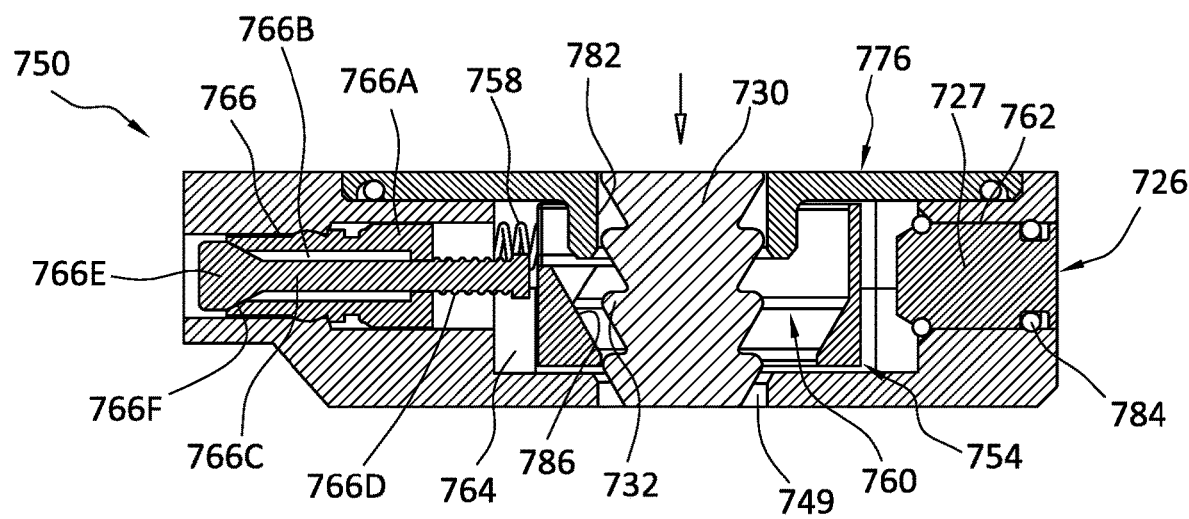
FIG. 15B shows a detail view of the cross section of the prosthetic lock assembly of FIG. 15A.

Engagement between the locking device 754 and the attachment pin 730 moves the prosthetic lock assembly 706 toward a loading position when the attachment pin 730 is partially inserted in the pin hole 760 of the lock body 750 as shown in FIGS. 15A and 15B.

In the loading position, the attachment pin 730 engages with the pin engagement part 786 of the locking device 754 as the attachment pin 730 moves through the pin hole 760, which, in turn, pushes the locking device 754 in a first direction or away from the release mechanism 726 and toward the valve assembly 766. The pin engagement part 786 can comprise an inclined or conical upper surface so that sliding contact between the attachment pin 730 and the upper surface of the pin engagement part 786 drives the locking device 754 in the first direction.

As the locking device 754 moves in the first direction, the locking device 754 compresses the spring members 758 between the locking device 754 and the lock body 750. The valve assembly 766 is initially in the closed position, preventing air from entering the chamber 764 via the valve assembly 766. According to a variation, as the attachment pin 730 is inserted in the lock body 750, a pressure increase in the chamber 764 can open the one-way valve 770, expelling air out of the prosthetic lock assembly 706. In the locked position, the locking device 754 can be disengaged from both the release mechanism 726 and the valve assembly 766.

Figure 16A:
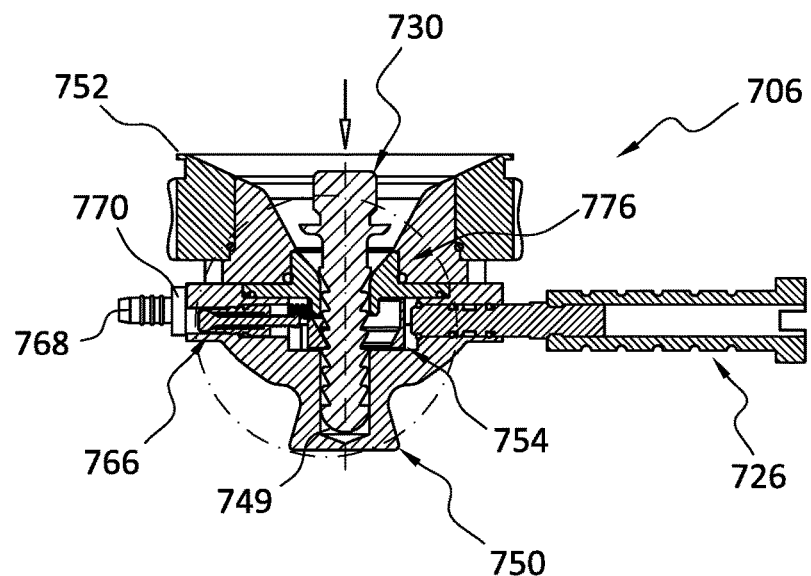
FIG. 16A shows a cross section in an elevational view of the prosthetic lock assembly of FIG. 12 in a third position.
Figure 16B:
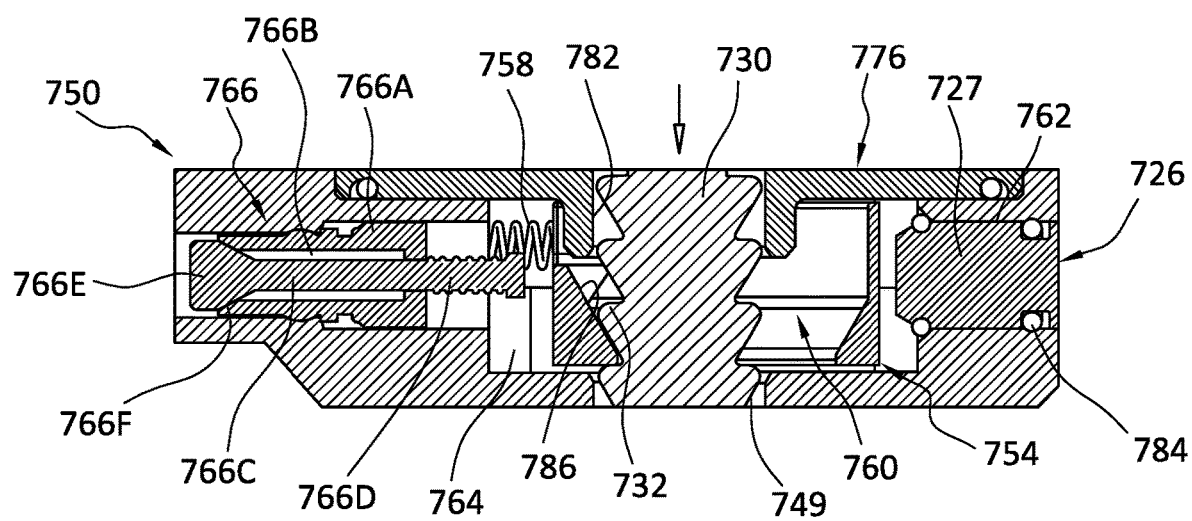
FIG. 16B shows a detail view of the cross section of the prosthetic lock assembly of FIG. 16A.

Referring to FIGS. 16A and 16B, when the pin engagement part 786 is aligned between adjacent serrations 732 on the attachment pin 730 and/or the attachment pin 730 is fully inserted in the pin hole 760, the prosthetic lock assembly 706 can move to a locked position. In the locked position, stored energy in the spring members 758 forces the locking device 754 in a second direction opposite the first direction or toward the attachment pin 730, which, in turn, drives the pin engagement part 786 in a corresponding space between adjacent serrations 732 on the attachment pin 730. This engagement of the pin engagement part 786 between the serrations 732 locks the attachment pin 730 in the prosthetic lock assembly 706, forming a mechanical lock between the prosthetic liner 704 and the socket 702. It will be appreciated that the distribution of the serrations 732 along a length of the attachment pin 730 allows the locking device 754 to lock the attachment pin 730 in the lock body 750 at different positions or heights. The locking device 754 can be disengaged from both the release mechanism 726 and the valve assembly 766 in the locked position.

Optionally, the prosthetic lock assembly 706 can be arranged to provide a user feedback when the prosthetic lock assembly 706 moves into the locked position. For instance, a hardness of the pin engagement part 786 or the attachment pin 730 can be selected to produce a click or knock when the pin engagement part 786 contacts the attachment pin 730 between adjacent serrations 732, providing feedback to the user that the prosthetic liner 704 is correctly or securely positioned in the socket 702. While the attachment pin 730 is described as including serrations 732, in other embodiments, the locking device 754 can be arranged to selectively interact with and lock an attachment pin having a flat, smooth, or other configuration.

With the prosthetic lock assembly 706 is in the locked position, the one-way valve 768 can facilitate the creation of a vacuum lock in the suspension region B. For instance, a pump system can be fluidly connected to the suspension region B via the one-way valve 768 on the lock body 750 and operated to create an elevated vacuum environment in the suspension region B, which, in turn, can form a vacuum lock between the socket 702 and the prosthetic liner 704 in addition to the mechanical lock between the residual limb and the socket 702. The pump system can be connected to the one-way valve 768 via a tube or in any other suitable manner.

Figure 17A:
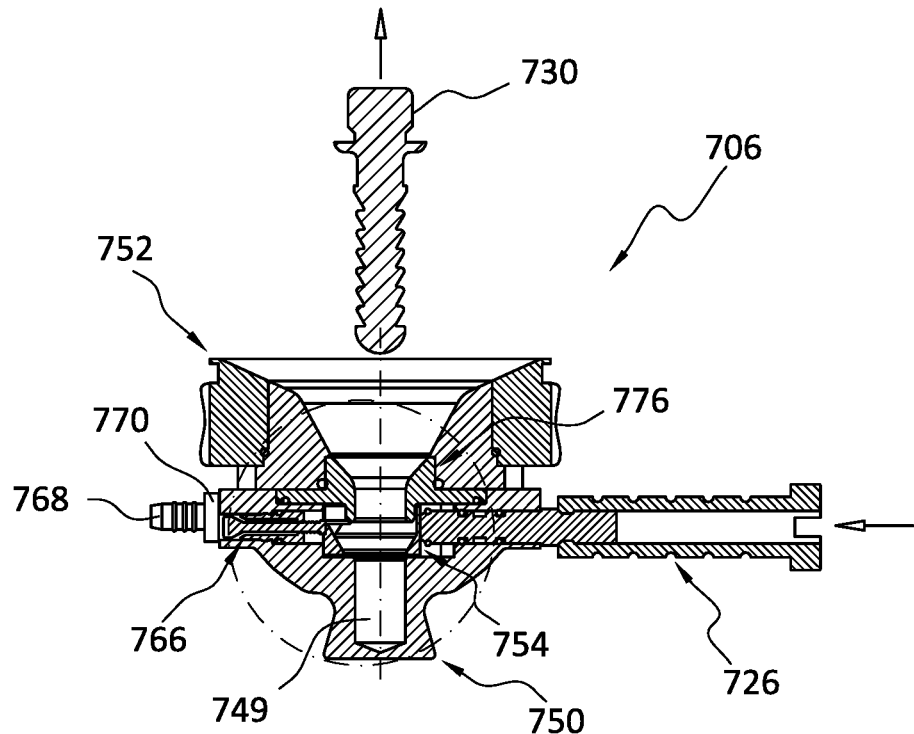
FIG. 17A shows a cross section in an elevational view of the prosthetic lock assembly of FIG. 12 in a fourth position.
Figure 17B:
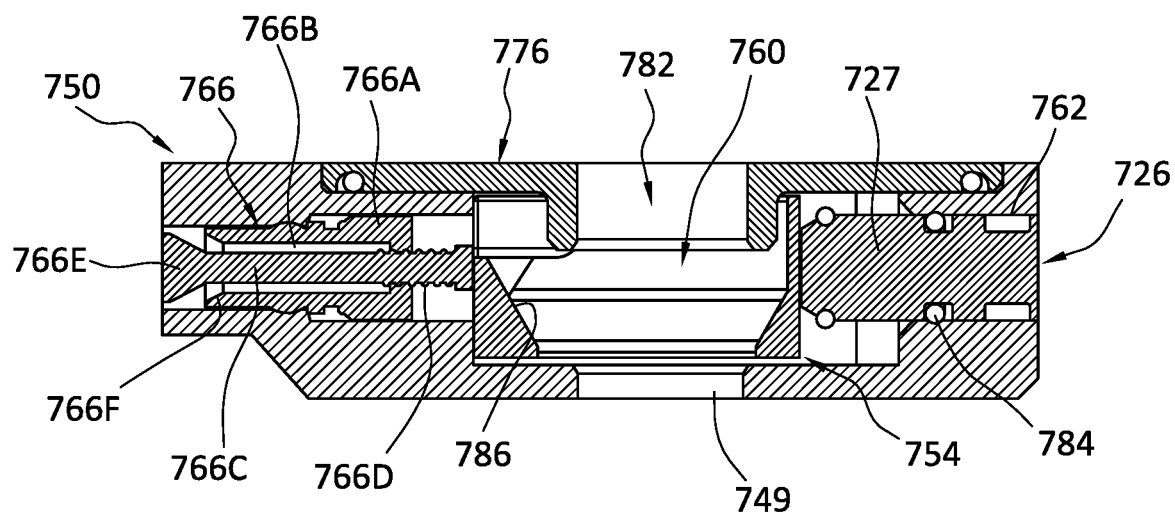
FIG. 17B shows a detail view of the cross section of the prosthetic lock assembly of FIG. 17A.

Referring to FIGS. 17A and 17B, the release mechanism 726 can move the prosthetic lock assembly 706 to a release position in which the mechanical lock and the vacuum lock are released. In use, the release mechanism 726 may be pushed into the lock body 750 so that the rod 727 urges the locking device 754 in the first direction or toward the valve assembly 766, which, in turn, disengages the pin engagement part 786 from between a space between adjacent serrations 732 on the attachment pin 730. This allows upward axial movement of the attachment pin 730 within the prosthetic lock assembly 706, releasing the mechanical lock.

As the rod 727 urges the locking device 754 further in the first direction, the locking device 754 can engage with and drive the pin member 766C of the valve assembly 766 toward the valve housing 766A, which, in turn, separates the head portion 766E of the pin member 766C from the seat 766F of the valve housing 766A. This moves the valve assembly 766 to the open position, allowing air to enter the suspension region B via the valve assembly 766, releasing the vacuum lock.

The prosthetic lock assembly 706 is preferably arranged such that the release mechanism 726 releases the mechanical lock between the locking device 754 and the attachment pin 730 before releasing the vacuum lock in the suspension region B. More particularly, the rod 727 may be pushed into the lock body 750 to first urge the locking device 754 in the first direction away from the attachment pin 730, releasing the mechanical lock, and then to urge the head portion 766E of the pin member 766C away from a seat 766F defined by the valve body 766A, allowing air to enter the chamber 764 via the valve assembly 766, which is then able to travel through the opening 782 which is now open because of the attachment pin 730 being moved.

The release mechanism 726 can thus release the mechanical and vacuum locks of the prosthetic socket system 700 with a single action. This beneficially facilitates doffing of the socket 702 as good hand dexterity and/or strength are not required to operate the prosthetic lock assembly 706. Rather, the prosthetic liner 704 can be securely attached to the socket 702 and easily released from the socket 702 with a simple manipulation of the release mechanism 726. When the release mechanism 726 moves the valve assembly 766 to the open position, the spring members 758 are further compressed relative to the compression of the spring members 758 in the locked position.

When the attachment pin 730 is removed from the lock body 750 and the release mechanism 726 is released, stored energy in the spring members 758 forces the locking device 754 back in the second direction, returning the prosthetic lock assembly 706 toward the unloaded position. Simultaneously or near simultaneously, stored energy in the spring member 766D on the pin member 766C forces the valve assembly 766 toward the closed position, resealing the chamber 764 and the consequently suspension region B.

According to a variation, the prosthetic lock assembly 706 can move to a mechanical release only position. For example, the rod 727 of the release mechanism 726 may be pushed into the lock body 750 a selected distance to urge the locking device 754 in the first direction away from the attachment pin 730, thereby disengaging the pin engagement part 786 from the serrations 732 of the attachment pin 730, but short of an actuating engagement with the pin member 766B of the valve assembly 766, leaving the valve assembly 766 in the closed position. This allows the prosthetic socket system 700 to release the mechanical lock between the prosthetic liner 704 and the socket 702 when the release mechanism 726 is partially depressed without releasing the vacuum lock. Such an arrangement can reduce the likelihood of the socket 702 unexpectedly falling off the residual limb due to accidental contact with the release mechanism 726, and allows a user to easily and intuitively use the prosthetic socket system 700 according to their particular needs at any given time.

The prosthetic lock assembly 706 thus controls mechanical and vacuum suspension in the prosthetic socket system 700, providing more secure and reliable suspension to a user. Further, the release mechanism 726 is operable to release both the mechanical lock between the attachment pin 730 and the locking device 754, and the vacuum lock in the suspension region B in a single action. Moreover, the release mechanism 726 can release the mechanical lock of the prosthetic socket system 700 prior to releasing the vacuum lock, improving user safety.

Figure 18:
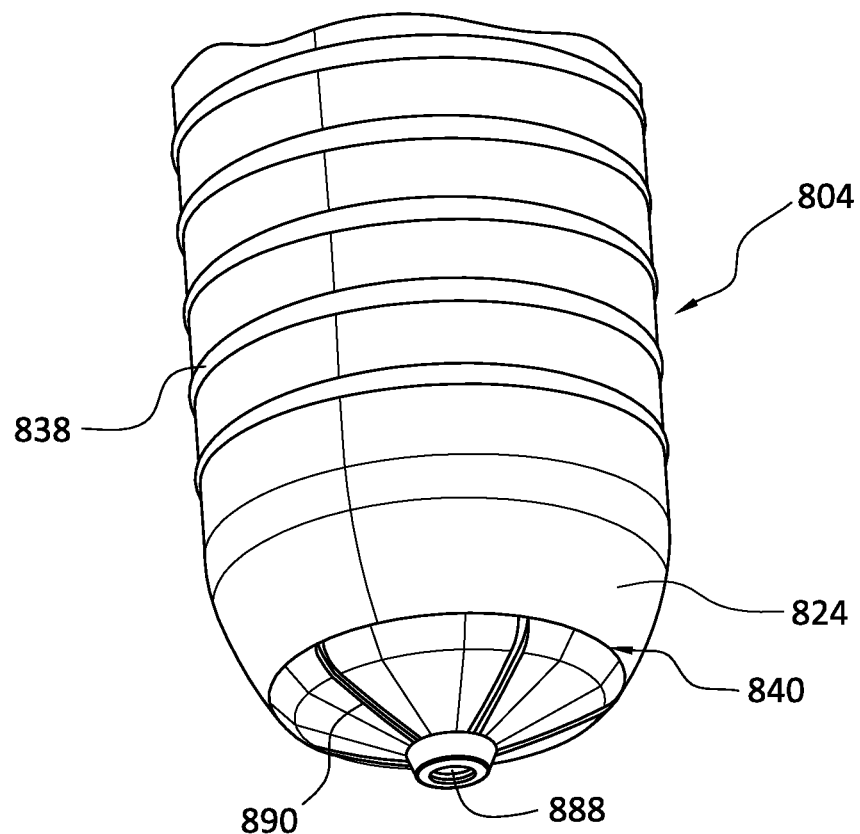
FIG. 18 shows a prosthetic view of a prosthetic socket system according to another embodiment.
Figure 19:
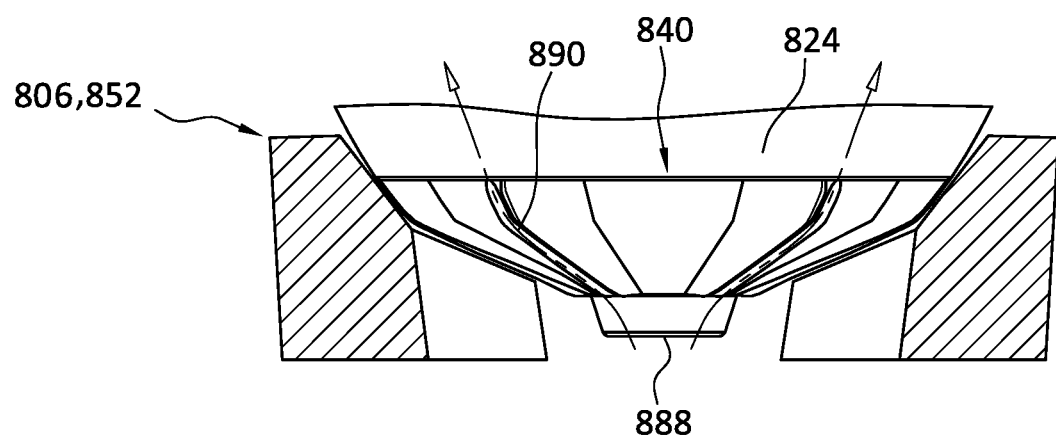
FIG. 19 shows a partial detailed view of the prosthetic liner of FIG. 18.
Figure 20:
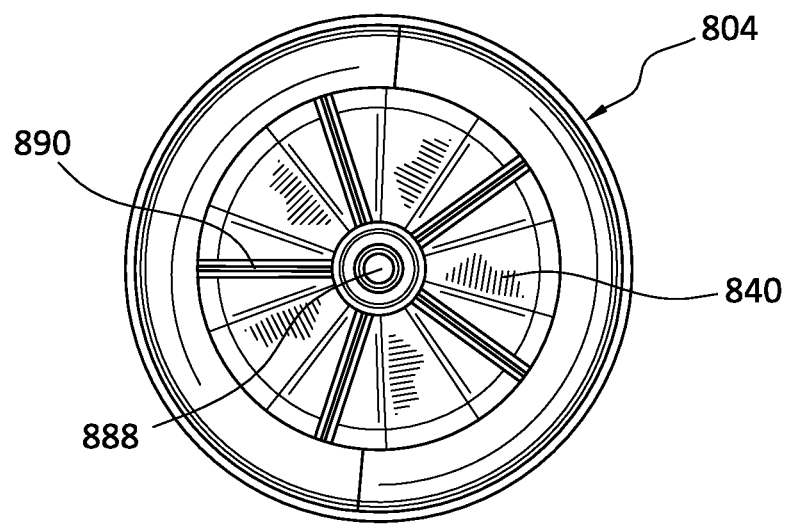
FIG. 20 shows a bottom view of the prosthetic liner of FIG. 18.

FIGS. 18-20 illustrate yet another embodiment of prosthetic liner 804 of the present disclosure. The prosthetic liner 804 includes a liner body having a proximal end, which is open, and a distal end 824 which is closed. The liner body defines an inner surface that interfaces with the skin, and an outer surface opposing the inner surface. The outer surface can include a plurality of seal bands 838 arranged to frictionally engage with a movable seal component positionable on the prosthetic liner 804. The distal end 824 includes an umbrella 840 that can be attached to or integrated with the distal end 824 of the prosthetic liner 804. The umbrella 840 is arranged to mount an attachment pin to the distal end 824 via a stem portion defining a threaded opening 888.

As discussed above, when the attachment pin is inserted in a prosthetic lock assembly 806 of the present disclosure, the umbrella 840 may interact with a mounting plate 852 of the prosthetic lock assembly 806. In certain devices, this interaction between the umbrella 840 and the mounting plate 852 can cause the umbrella 840 to seal or stick against the prosthetic lock assembly 806. Disadvantageously, this can interfere with or prevent a vacuum in a suspension region between the socket and the prosthetic liner 804 because air cannot move between the umbrella 840 and the prosthetic lock assembly 806, such as when air or other fluid is being evacuated from the space between the prosthetic liner and the socket.

In the illustrated embodiment, the distal end 824 of the prosthetic liner 804 defines a plurality of flow channels 890. In the illustrated embodiment, the flow channels 890 can be distributed circumferentially about the distal end 824 and extend generally in a radial direction along the distal end 824. Other configurations, paths, and shapes are possible. The flow channels 890 can be defined in the umbrella 840. The flow channels 890 can be generally linear. The flow channels 890 can comprise recesses defined in the distal end 824, or alternatively may comprise protruding portions formed in the distal end 824.

When the prosthetic liner 804 is positioned in a socket and on the prosthetic lock assembly 806, the flow channels 890 define flow paths along the surface of the distal end 824 into which air or other fluids can flow between the suspension region in the socket and a chamber of the prosthetic lock assembly 806 as seen in FIG. 19. This improved flow of fluid (e.g., air) between the distal end 824 and the prosthetic lock assembly 806 helps prevent the distal end 824 from sealing or sticking on the prosthetic lock assembly 806, which, in turn, allows the prosthetic lock assembly 806 to more effectively and timely build up and release vacuum or a vacuum lock in the suspension region.

Figure 21:
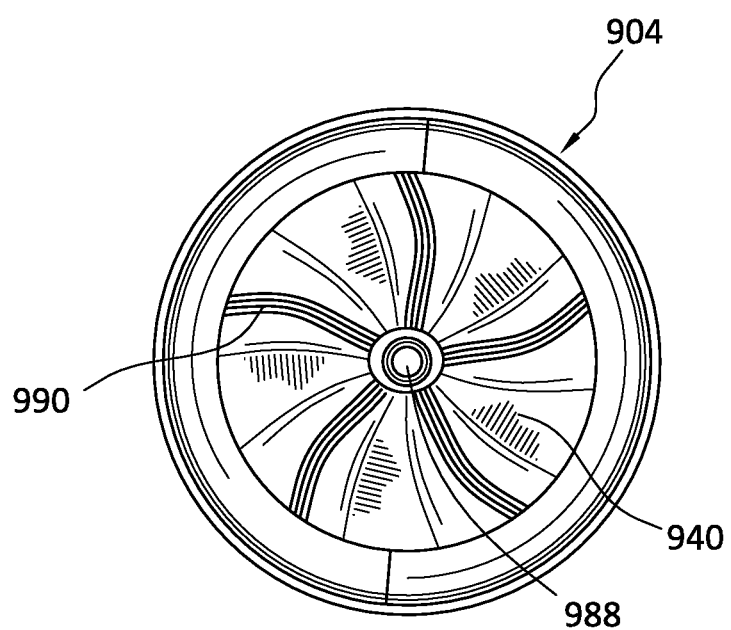
FIG. 21 shows a bottom view of a prosthetic liner according to another embodiment.

FIG. 21 illustrates yet another embodiment of a prosthetic liner 904 according to the present disclosure including a plurality of flow channels 990. As seen, a distal end of the prosthetic liner 904 includes an umbrella 940 defining the flow channels 990. The flow channels 990 are distributed circumferentially about the umbrella 940 and extend generally in a radial direction. The flow channels 990 can extend completely or partially between a stem portion 988 of the umbrella 940 and an outer edge of the umbrella 940. In other embodiments, the flow channels 990 can be distributed about only a portion of the umbrella 940 or the distal end.

As seen in the depicted embodiment, the flow channels 990 can curve along a length of the flow channels 900 and/or along a length or location of the umbrella 940. According to a variation, the flow channels 990 can have a branched configuration including primary segments and secondary segments branching from the primary segments, allowing the flow channels 990 to extend in different directions. The primary segments can be fluidly connected to the outer edge of the umbrella 940. The primary and second segments can have varying cross-sectional areas. For instance, the primary segments can have a larger cross-sectional area than the secondary segments extending from the primary segments, varying the flow rate and/or flow velocity of air or other fluid moving through the flow channels 990.

Like above, the flow channels 990 improve fluid flow between the distal end 924 and a prosthetic lock assembly, which, in turn, allows the prosthetic lock assembly to more effectively build up and release vacuum in a suspension region defined between the prosthetic liner 904 and a socket. The inclusion of primary and secondary segments allows for fluid to be effectively and evenly removed from a suspension region while minimizing the overall volume and profile of the flow channels 990 within the umbrella 940 and between the prosthetic liner and the socket.

By providing a prosthetic system comprising a combination of mechanical and vacuum locks according to embodiments of the disclosure, a user may benefit from an enhanced attachment between the prosthetic liner and a prosthetic socket, combining the strength and stability, for example, of a mechanical lock with the comfort and added security of a vacuum lock or seal, while also mitigating the downsides associated with each type of attachment, such as "milking," "pistoning," and associated ailments. This arrangement benefits a wide number of user needs and conditions, and also offers a simple, intuitive, and reliable method for donning and doffing the prosthetic socket system. The prosthetic socket system is further adapted to conveniently and simply be arranged with existing and/or conventional liners and sockets, for added versatility and reduced cost.

It is to be understood that not necessarily all objects or advantages may be achieved under any embodiment of the disclosure. Those skilled in the art will recognize that the prosthetic socket system may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of skill in this art to construct a prosthetic socket system in accordance with principles of the present disclosure. It will be understood by the skilled artisan that the features described herein may apply to other types of orthopedic, prosthetic, or medical devices.

Although this disclosure describes certain exemplary embodiments and examples of a prosthetic socket system, it nevertheless will be understood by those skilled in the art that the present disclosure extends beyond the specifically disclosed prosthetic socket embodiments to other alternative embodiments and/or users of the disclosure and obvious modifications and equivalents thereof. It is intended that the scope of the present disclosure should not be limited by the particular disclosed embodiments described above, and may be extended to prosthetic devices and supports, and other applications that may employ the features described herein.

The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic system, comprising a prosthetic liner, comprising:
   a liner body having an open proximal end, and a closed distal end along a liner body axis;
   an attachment pin extending from the distal end of the liner body; and
   a sealing system including a first seal component arranged to form a seal around the attachment pin and seal against an interior surface of a prosthetic socket, the first seal component including a base surrounding the attachment pin and a sealing portion, the base defines a neck extending from a central portion of the base and directed distally along the liner body axis, the neck forming an opening therethrough through which the attachment pin extends, the sealing portion forming a wall segment extending circumferentially about the attachment pin;
   wherein the wall segment has an outer wall forming an outer peripheral portion of the wall segment and directed distally from a connection point with an inner wall of the wall segment toward the liner body axis with a diameter decreasing distally, and the wall segment defines the inner wall with a conical configuration with a decreasing diameter extending toward its distal end about the liner body axis, the outer wall and the inner wall securing to one another at a maximum diameter of the inner wall and at a proximally-most location of the inner wall at the connection point, the outer wall and the inner wall are arranged at different angles relative to one another such that a variable clearance is defined between the inner wall and the outer wall, the variable clearance increasing in the distal direction relative to the liner body axis.

2. The prosthetic system of claim 1, wherein a rigid part is associated with the neck, the rigid part includes a support base defining a central opening and an annular wall about the support base, the rigid part being more rigid than the sealing portion.

3. The prosthetic system of claim 2, wherein the distal end of the liner body includes an umbrella enabling interconnection between the liner body and the prosthetic socket, the rigid part being arranged to transfer forces between the attachment pin and the umbrella and away from the sealing portion.

4. The prosthetic system of claim 1, wherein the neck extends distally from the base along the liner body axis beyond where the sealing portion extends.

5. The prosthetic system of claim 4, wherein the neck commences and extends distally generally from a location whereat the wall segment terminates distally.

6. The prosthetic system of claim 1, wherein the sealing portion is arranged to engage the interior surface of the prosthetic socket, a flexibility of the sealing portion is arranged to deflect toward the prosthetic liner and deform to form the seal between the prosthetic liner and the interior surface of the prosthetic socket such that the variable clearance and flexibility of the first seal component to compensate for relative movement between the prosthetic socket and the prosthetic liner.

7. The prosthetic system of claim 1, wherein a plurality of blades extend between the inner wall and the outer wall within the variable clearance and about the attachment pin.

8. The prosthetic system of claim 7, wherein each blade of the plurality of blades is arranged at an oblique angle relative to the liner body axis.

9. The prosthetic system of claim 7, wherein the plurality of blades are confined within the variable clearance.

10. The prosthetic system of claim 9, wherein the variable clearance is located proximally relative to the neck and relative to the liner body axis.

11. The prosthetic system of claim 1, further comprising a second seal component extending circumferentially about the liner body at a location along the liner body axis proximal relative to the first seal component and spaced apart from the first seal component.

* * * * *